(12) United States Patent
Boit et al.

(10) Patent No.: US 9,211,378 B2
(45) Date of Patent: Dec. 15, 2015

(54) METHODS AND SYSTEMS FOR DOSING A MEDICAMENT

(75) Inventors: Christopher S. Boit, Wellesley, MA (US); Peter Gravesen, Nordborg (DK); Heiko Arndt, Flensborg (DE); Gregory H. Peatfield, Atkinson, NH (US); Patrick F. McDermott, Oxford, MA (US)

(73) Assignee: CEQUR SA, Horw (CH)

( * ) Notice: Subject to any disclaimer, the term of this patent is extended or adjusted under 35 U.S.C. 154(b) by 523 days.

(21) Appl. No.: 12/910,437

(22) Filed: Oct. 22, 2010

(65) Prior Publication Data

US 2012/0101451 A1 Apr. 26, 2012

(51) Int. Cl.
| A61M 5/142 | (2006.01) |
| A61M 5/315 | (2006.01) |
| A61M 5/14 | (2006.01) |
| A61M 5/148 | (2006.01) |
| A61M 5/168 | (2006.01) |
| A61M 5/31 | (2006.01) |
| A61M 39/22 | (2006.01) |

(52) U.S. Cl.
CPC ......... *A61M 5/14248* (2013.01); *A61M 5/1424* (2013.01); *A61M 5/141* (2013.01); *A61M 5/148* (2013.01); *A61M 5/1413* (2013.01); *A61M 5/16809* (2013.01); *A61M 5/3153* (2013.01); *A61M 5/3157* (2013.01); *A61M 2005/3123* (2013.01); *A61M 2039/224* (2013.01); *A61M 2205/3331* (2013.01); *A61M 2205/581* (2013.01); *A61M 2205/582* (2013.01); *A61M 2205/583* (2013.01)

(58) Field of Classification Search
CPC . A61M 5/141; A61M 5/142; A61M 5/14212; A61M 5/14216; A61M 5/1424; A61M 5/14248; A61M 5/14252; A61M 5/16809; A61M 5/204; A61M 5/3153; A61M 5/3157; A61M 2005/3114; A61M 2005/3115; A61M 2205/58; A61M 2205/581; A61M 2205/582; A61M 2205/583
USPC ............. 604/82–92, 183, 186, 218, 224, 246, 604/247, 890.1; 417/374, 490
See application file for complete search history.

(56) References Cited

U.S. PATENT DOCUMENTS

| 3,895,741 A | 7/1975 | Nugent et al. |
| 4,055,175 A | 10/1977 | Clemens et al. |

(Continued)

FOREIGN PATENT DOCUMENTS

| CN | 1209073 A | 2/1999 |
| DE | 42 00 595 | 7/1993 |

(Continued)

OTHER PUBLICATIONS

European Search Report for Application No. EP08013595 published Sep. 23, 2009.

(Continued)

*Primary Examiner* — Kami A Bosworth
(74) *Attorney, Agent, or Firm* — Goodwin Procter LLP

(57) ABSTRACT

A manually actuated pump, such as a bolus delivery circuit of an insulin pump, combines a direct drive piston system with a lost motion valve system, to deliver reliably a full bolus dose, while precluding partial dosing or inadvertent overdosing conditions. The pump may also include a signaling device to indicate when a full bolus dose is delivered.

25 Claims, 23 Drawing Sheets

(56) References Cited

U.S. PATENT DOCUMENTS

| | | | |
|---|---|---|---|
| 4,077,405 | A | 3/1978 | Haerten et al. |
| 4,086,036 | A | 4/1978 | Hagen et al. |
| 4,193,397 | A | 3/1980 | Tucker et al. |
| 4,209,014 | A | 6/1980 | Sefton et al. |
| 4,237,775 | A | 12/1980 | Eisele |
| 4,265,241 | A | 5/1981 | Portner et al. |
| 4,431,425 | A | 2/1984 | Thompson et al. |
| 4,435,173 | A | 3/1984 | Siposs et al. |
| 4,443,218 | A | 4/1984 | DeCant, Jr. et al. |
| 4,447,224 | A | 5/1984 | DeCant, Jr. et al. |
| 4,486,190 | A | 12/1984 | Reinicke |
| 4,525,165 | A | 6/1985 | Fischell |
| 4,551,133 | A | 11/1985 | Zegers de Beyl et al. |
| 4,557,726 | A | 12/1985 | Reinicke |
| 4,569,675 | A | 2/1986 | Prosl et al. |
| 4,575,041 | A | 3/1986 | Hu |
| 4,604,089 | A | 8/1986 | Santangelo et al. |
| 4,617,014 | A | 10/1986 | Cannon et al. |
| 4,671,320 | A | 6/1987 | Grifols et al. |
| 4,714,462 | A | 12/1987 | DiDomenico |
| 4,715,852 | A | 12/1987 | Reinicke et al. |
| 4,730,635 | A | 3/1988 | Linden |
| 4,752,289 | A | 6/1988 | Balding et al. |
| 4,755,173 | A | 7/1988 | Konopka et al. |
| 4,784,577 | A | 11/1988 | Ritson et al. |
| 4,784,645 | A | 11/1988 | Fischell |
| 4,820,273 | A | 4/1989 | Reinicke |
| 4,828,551 | A | 5/1989 | Gertler et al. |
| 4,836,752 | A | 6/1989 | Burkett |
| 4,868,585 | A | 9/1989 | Nishikawa et al. |
| 4,886,499 | A | 12/1989 | Cirelli et al. |
| 4,898,579 | A | 2/1990 | Groshong et al. |
| 4,920,972 | A | 5/1990 | Frank et al. |
| 4,931,050 | A | 6/1990 | Idriss |
| 4,943,279 | A | 7/1990 | Samiotes et al. |
| 4,994,035 | A | 2/1991 | Mokros |
| 4,998,918 | A | 3/1991 | Mimura et al. |
| 5,011,477 | A | 4/1991 | Winchell et al. |
| 5,033,714 | A | 7/1991 | Winchell et al. |
| 5,034,004 | A | 7/1991 | Crankshaw |
| 5,085,644 | A | 2/1992 | Watson et al. |
| 5,088,983 | A | 2/1992 | Burke |
| 5,096,385 | A | 3/1992 | Georgi et al. |
| 5,152,753 | A | 10/1992 | Laguette et al. |
| 5,176,358 | A | 1/1993 | Bonne et al. |
| 5,176,662 | A | 1/1993 | Bartholomew et al. |
| 5,178,609 | A | 1/1993 | Ishikawa et al. |
| 5,190,522 | A | 3/1993 | Wojcicki et al. |
| 5,192,272 | A | 3/1993 | Faure et al. |
| 5,211,626 | A | 5/1993 | Frank et al. |
| 5,211,632 | A | 5/1993 | Tsukada et al. |
| 5,224,934 | A | 7/1993 | Payne et al. |
| 5,241,985 | A | 9/1993 | Faust et al. |
| 5,248,301 | A | 9/1993 | Koenig, Jr. et al. |
| 5,257,980 | A | 11/1993 | Van Antwerp et al. |
| 5,279,586 | A | 1/1994 | Balkwill |
| 5,304,153 | A | 4/1994 | Tsujikawa et al. |
| 5,317,269 | A | 5/1994 | Mills et al. |
| 5,321,392 | A | 6/1994 | Skakoon et al. |
| 5,346,372 | A | 9/1994 | Naruse et al. |
| 5,360,411 | A | 11/1994 | Mimura et al. |
| 5,395,320 | A | 3/1995 | Padda et al. |
| 5,492,533 | A | 2/1996 | Kriesel |
| 5,522,799 | A | 6/1996 | Furukawa |
| 5,524,907 | A | 6/1996 | Walser |
| 5,575,770 | A | 11/1996 | Melsky et al. |
| 5,584,813 | A | 12/1996 | Livingston et al. |
| 5,625,151 | A | 4/1997 | Yamaguchi |
| 5,681,284 | A | 10/1997 | Herskowitz |
| 5,720,721 | A | 2/1998 | Dumas et al. |
| 5,762,632 | A | 6/1998 | Whisson et al. |
| 5,764,034 | A | 6/1998 | Bowman et al. |
| 5,791,880 | A | 8/1998 | Wilson |
| 5,839,467 | A | 11/1998 | Saaski et al. |
| 5,843,014 | A | 12/1998 | Lattin et al. |
| 5,851,197 | A | 12/1998 | Marano et al. |
| 5,857,661 | A | 1/1999 | Amada et al. |
| 5,871,478 | A | 2/1999 | Berrigan et al. |
| 5,897,530 | A | 4/1999 | Jackson |
| 5,925,017 | A | 7/1999 | Kriesel et al. |
| 5,931,814 | A | 8/1999 | Alex et al. |
| 5,961,488 | A | 10/1999 | Barak et al. |
| 5,984,894 | A | 11/1999 | Poulsen et al. |
| 5,993,425 | A | 11/1999 | Kriesel |
| 5,997,501 | A | 12/1999 | Gross et al. |
| 6,009,752 | A | 1/2000 | Iwata |
| 6,045,533 | A | 4/2000 | Kriesel et al. |
| 6,068,751 | A | 5/2000 | Neukermans |
| 6,090,068 | A | 7/2000 | Chanut et al. |
| 6,126,642 | A | 10/2000 | Kriesel et al. |
| 6,159,188 | A | 12/2000 | Laibovitz et al. |
| 6,213,151 | B1 | 4/2001 | Jacobson et al. |
| 6,358,225 | B1 | 3/2002 | Butterfield |
| 6,406,276 | B1 | 6/2002 | Normand et al. |
| 6,416,291 | B1 | 7/2002 | Butterfield et al. |
| 6,416,495 | B1 | 7/2002 | Kriesel et al. |
| 6,471,675 | B1 | 10/2002 | Rogers et al. |
| 6,485,461 | B1 | 11/2002 | Mason et al. |
| 6,520,938 | B1 | 2/2003 | Funderburk et al. |
| 6,555,986 | B2 | 4/2003 | Moberg |
| 6,579,267 | B2 | 6/2003 | Lynch et al. |
| 6,585,707 | B2 | 7/2003 | Cabiri et al. |
| 6,589,229 | B1 | 7/2003 | Connelly et al. |
| 6,607,509 | B2 | 8/2003 | Bobroff et al. |
| 6,620,138 | B1 | 9/2003 | Marrgi et al. |
| 6,620,151 | B2 | 9/2003 | Blischak et al. |
| 6,641,566 | B2 | 11/2003 | Douglas et al. |
| 6,647,860 | B2 | 11/2003 | Savel et al. |
| 6,656,158 | B2 | 12/2003 | Mahoney et al. |
| 6,656,159 | B2 | 12/2003 | Flaherty |
| 6,659,980 | B2 | 12/2003 | Moberg et al. |
| 6,659,982 | B2 | 12/2003 | Douglas et al. |
| 6,666,845 | B2 | 12/2003 | Hooper et al. |
| 6,669,669 | B2 | 12/2003 | Flaherty et al. |
| 6,692,457 | B2 | 2/2004 | Flaherty |
| 6,699,218 | B2 | 3/2004 | Flaherty et al. |
| 6,702,779 | B2 | 3/2004 | Connelly et al. |
| 6,723,072 | B2 | 4/2004 | Flaherty et al. |
| 6,730,060 | B1 | 5/2004 | Steinbach et al. |
| 6,740,059 | B2 | 5/2004 | Flaherty |
| 6,749,587 | B2 | 6/2004 | Flaherty |
| 6,768,425 | B2 | 7/2004 | Flaherty et al. |
| 6,796,956 | B2 | 9/2004 | Hartlaub et al. |
| 6,802,823 | B2 | 10/2004 | Mason |
| 6,830,558 | B2 | 12/2004 | Flaherty et al. |
| 6,830,562 | B2 | 12/2004 | Mogensen et al. |
| 6,852,094 | B2 | 2/2005 | Beck et al. |
| 6,852,104 | B2 | 2/2005 | Blomquist |
| 6,871,546 | B2 | 3/2005 | Scheurich et al. |
| 6,892,755 | B2 | 5/2005 | Black |
| 6,901,293 | B2 | 5/2005 | Rogers et al. |
| 6,926,694 | B2 | 8/2005 | Marano-Ford et al. |
| 6,936,026 | B2 | 8/2005 | Diermann et al. |
| 6,960,192 | B1 | 11/2005 | Flaherty et al. |
| D515,288 | S | 2/2006 | Della Valle et al. |
| 6,997,907 | B2 | 2/2006 | Safabash et al. |
| 7,000,806 | B2 | 2/2006 | Py et al. |
| 7,018,360 | B2 | 3/2006 | Flaherty et al. |
| 7,029,455 | B2 | 4/2006 | Flaherty |
| 7,066,031 | B2 | 6/2006 | Zdeblick et al. |
| 7,109,878 | B2 | 9/2006 | Mann et al. |
| 7,137,964 | B2 | 11/2006 | Flaherty |
| 7,144,384 | B2 | 12/2006 | Gorman et al. |
| 7,150,741 | B2 | 12/2006 | Erickson et al. |
| 7,207,345 | B2 | 4/2007 | Somerville |
| 7,207,974 | B2 | 4/2007 | Safabash et al. |
| 7,291,126 | B2 | 11/2007 | Shekalim et al. |
| 7,303,549 | B2 | 12/2007 | Flaherty et al. |
| 7,341,572 | B2 | 3/2008 | Bridle et al. |
| 7,377,907 | B2 | 5/2008 | Shekalim |
| 7,771,412 | B2 | 8/2010 | Anderson et al. |
| 7,887,505 | B2 | 2/2011 | Flaherty |
| 7,918,825 | B2 | 4/2011 | O'Connor et al. |
| 2002/0087147 | A1 | 7/2002 | Hooper et al. |

(56) References Cited

U.S. PATENT DOCUMENTS

| | | | |
|---|---|---|---|
| 2002/0107492 A1* | 8/2002 | Brach et al. | 604/296 |
| 2002/0161332 A1 | 10/2002 | Ramey | |
| 2002/0183693 A1 | 12/2002 | Peterson et al. | |
| 2003/0135159 A1 | 7/2003 | Daily et al. | |
| 2003/0204274 A1 | 10/2003 | Ullestad et al. | |
| 2004/0059316 A1 | 3/2004 | Smedegaard | |
| 2004/0133166 A1 | 7/2004 | Moberg et al. | |
| 2004/0153032 A1 | 8/2004 | Garribotto et al. | |
| 2004/0158207 A1 | 8/2004 | Hunn et al. | |
| 2004/0167464 A1 | 8/2004 | Ireland et al. | |
| 2004/0216103 A1 | 10/2004 | Burky et al. | |
| 2004/0249363 A1 | 12/2004 | Burke et al. | |
| 2005/0101932 A1 | 5/2005 | Cote et al. | |
| 2005/0124936 A1 | 6/2005 | Mogensen et al. | |
| 2005/0171512 A1 | 8/2005 | Flaherty | |
| 2005/0182366 A1 | 8/2005 | Vogt et al. | |
| 2005/0203461 A1 | 9/2005 | Flaherty et al. | |
| 2005/0238507 A1 | 10/2005 | Dilanni et al. | |
| 2005/0255003 A1 | 11/2005 | Summersgill et al. | |
| 2005/0266582 A1 | 12/2005 | Modlin et al. | |
| 2005/0267441 A1 | 12/2005 | Douglas | |
| 2006/0030836 A1 | 2/2006 | Lee et al. | |
| 2006/0041229 A1 | 2/2006 | Garibotto et al. | |
| 2006/0069382 A1 | 3/2006 | Pedersen | |
| 2006/0161108 A1 | 7/2006 | Mogensen et al. | |
| 2006/0178633 A1 | 8/2006 | Garibotto et al. | |
| 2006/0184121 A1 | 8/2006 | Brockman et al. | |
| 2006/0264835 A1 | 11/2006 | Nielsen et al. | |
| 2006/0282290 A1 | 12/2006 | Flaherty et al. | |
| 2007/0073243 A1* | 3/2007 | Bonney | 604/186 |
| 2007/0074722 A1 | 4/2007 | Giroux et al. | |
| 2007/0083153 A1 | 4/2007 | Haar | |
| 2007/0112301 A1 | 5/2007 | Preuthun et al. | |
| 2007/0118405 A1 | 5/2007 | Campbell et al. | |
| 2007/0231204 A1 | 10/2007 | Hyde et al. | |
| 2007/0250007 A1 | 10/2007 | Shekalim | |
| 2007/0272764 A1* | 11/2007 | Poulard | 239/71 |
| 2007/0299397 A1 | 12/2007 | Alferness et al. | |
| 2008/0033361 A1 | 2/2008 | Evans et al. | |
| 2008/0051710 A1 | 2/2008 | Moberg et al. | |
| 2008/0051738 A1 | 2/2008 | Griffin | |
| 2008/0086086 A1 | 4/2008 | Field et al. | |
| 2008/0116647 A1 | 5/2008 | Anderson et al. | |
| 2008/0119822 A1 | 5/2008 | Knauper | |
| 2008/0121657 A1* | 5/2008 | Voegele et al. | 222/137 |
| 2008/0139907 A1 | 6/2008 | Rao et al. | |
| 2008/0147044 A1 | 6/2008 | Palmer et al. | |
| 2008/0147050 A1 | 6/2008 | Mann et al. | |
| 2008/0160492 A1 | 7/2008 | Campbell et al. | |
| 2008/0172030 A1 | 7/2008 | Blomquist | |
| 2008/0183060 A1 | 7/2008 | Steil et al. | |
| 2008/0214919 A1 | 9/2008 | Harmon et al. | |
| 2008/0227210 A1 | 9/2008 | Smith | |
| 2008/0234630 A1 | 9/2008 | Iddan et al. | |
| 2008/0294094 A1 | 11/2008 | Mhatre et al. | |
| 2009/0012479 A1 | 1/2009 | Moller et al. | |
| 2009/0088690 A1 | 4/2009 | Carter | |
| 2009/0099521 A1 | 4/2009 | Gravesen et al. | |
| 2009/0112155 A1 | 4/2009 | Zhao et al. | |
| 2009/0112156 A1 | 4/2009 | Rush et al. | |
| 2009/0118669 A1 | 5/2009 | Bendek et al. | |
| 2009/0143732 A1 | 6/2009 | O'Connor et al. | |
| 2009/0177159 A1 | 7/2009 | Knopper et al. | |
| 2009/0216194 A1 | 8/2009 | Elgard Pedersen et al. | |
| 2009/0240240 A1 | 9/2009 | Hines et al. | |
| 2009/0270798 A1 | 10/2009 | Jones | |
| 2009/0299328 A1* | 12/2009 | Mudd et al. | 604/506 |
| 2009/0326457 A1 | 12/2009 | O'Connor | |
| 2010/0017141 A1 | 1/2010 | Campbell et al. | |
| 2010/0030198 A1 | 2/2010 | Beebe et al. | |
| 2011/0043357 A1 | 2/2011 | Peatfield et al. | |
| 2011/0046558 A1 | 2/2011 | Gravesen et al. | |

FOREIGN PATENT DOCUMENTS

| | | |
|---|---|---|
| EP | 0 039 124 | 11/1981 |
| EP | 0 239 721 | 7/1987 |
| EP | 0 267 041 | 5/1988 |
| EP | 0427588 | 5/1991 |
| EP | 0 239 244 | 9/1991 |
| EP | 0 562 694 | 9/1993 |
| EP | 0 450 186 | 2/1995 |
| EP | 0 646 381 | 4/1995 |
| EP | 0 960 626 | 12/1999 |
| EP | 1177802 | 2/2002 |
| EP | 1 254 676 A1 | 12/2003 |
| EP | 1 792 655 | 6/2007 |
| GB | 1029233 A | 5/1966 |
| GB | 2 031 558 | 4/1980 |
| GB | 2 197 691 | 5/1988 |
| JP | 56-136562 | 10/1981 |
| JP | 63-197464 | 8/1988 |
| JP | 3-165872 | 7/1991 |
| JP | 5-15590 | 1/1993 |
| JP | 8-206199 | 8/1996 |
| RU | 2129021 C1 | 4/1999 |
| WO | WO-92/16304 | 10/1992 |
| WO | WO-93/05832 A1 | 4/1993 |
| WO | WO-93/18305 | 9/1993 |
| WO | WO-9427669 A1 | 12/1994 |
| WO | WO-97/12665 A1 | 4/1997 |
| WO | WO-9738322 A1 | 10/1997 |
| WO | WO-99/01731 | 1/1999 |
| WO | WO-99/27985 | 6/1999 |
| WO | WO-99/44655 | 9/1999 |
| WO | WO-99/44740 A1 | 9/1999 |
| WO | WO-01/85233 | 11/2001 |
| WO | WO-02/070047 | 9/2002 |
| WO | WO-02068015 | 9/2002 |
| WO | WO-03068294 | 8/2003 |
| WO | WO-2006/032692 | 3/2006 |
| WO | WO-2007/057038 | 5/2007 |
| WO | WO-2008017329 | 2/2008 |
| WO | WO-2008024810 | 2/2008 |

OTHER PUBLICATIONS

International Search Report and Written Opinion mailed Jul. 20, 2011, for PCT Application PCT/US2010/044996, 18 pages.

International Search Report and Written Opinion mailed Mar. 5, 2012, for PCT Application PCT/US2011/057123, 12 pages.

International Search Report and Written Opinion mailed Mar. 9, 2012, for PCT Application PCT/US2011/057123, 12 pages.

Office Action with English translation in Chinese Patent Application No. 201180057819.6 dated Dec. 4, 2014 19 pages.

* cited by examiner

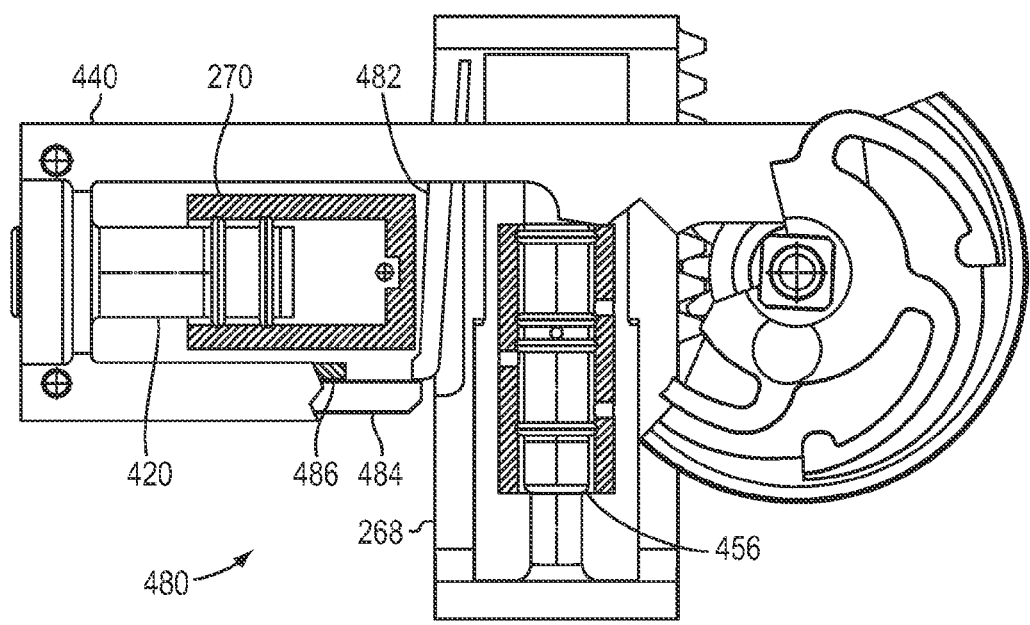
FIG. 15A1
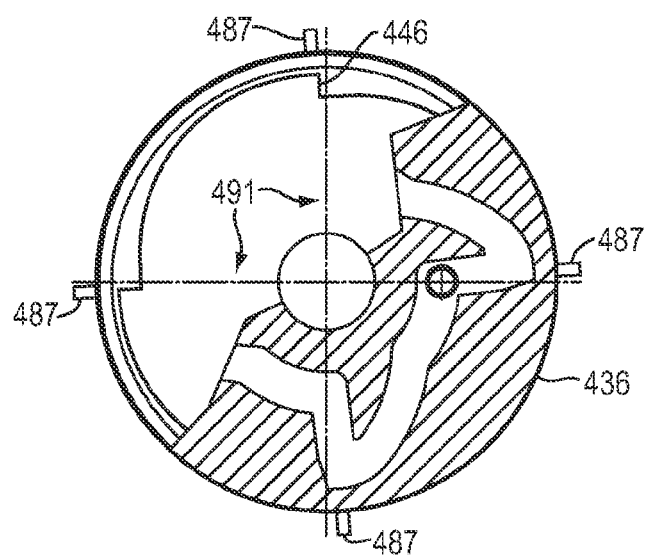
FIG. 15A2

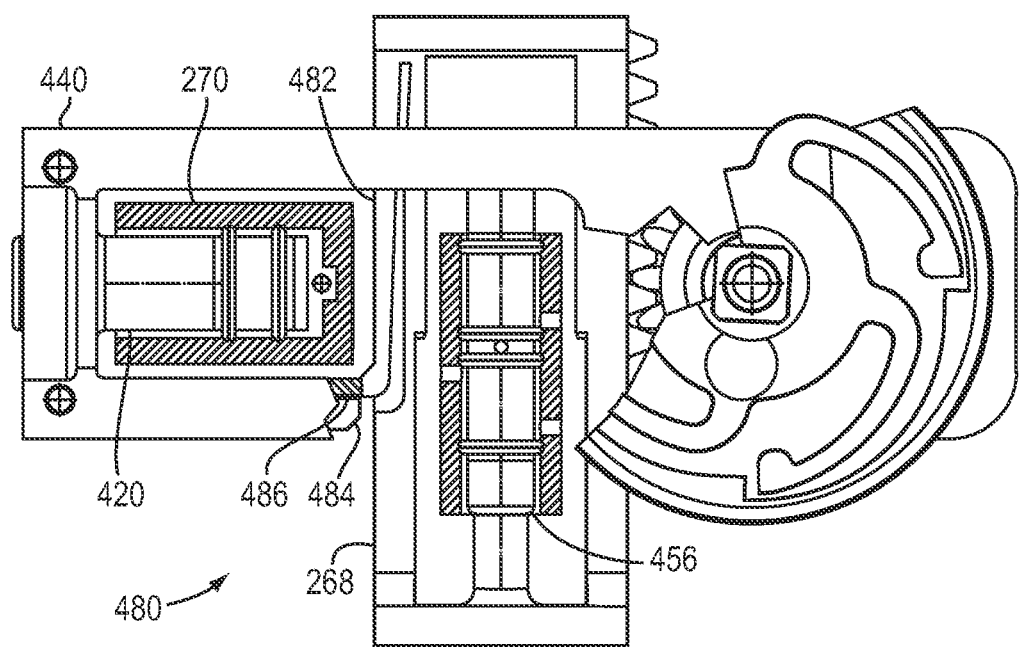
FIG. 16A1
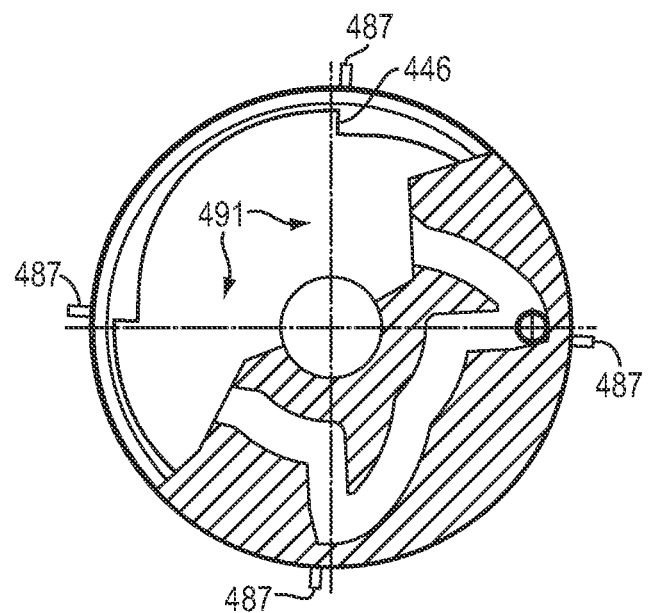
FIG. 16A2

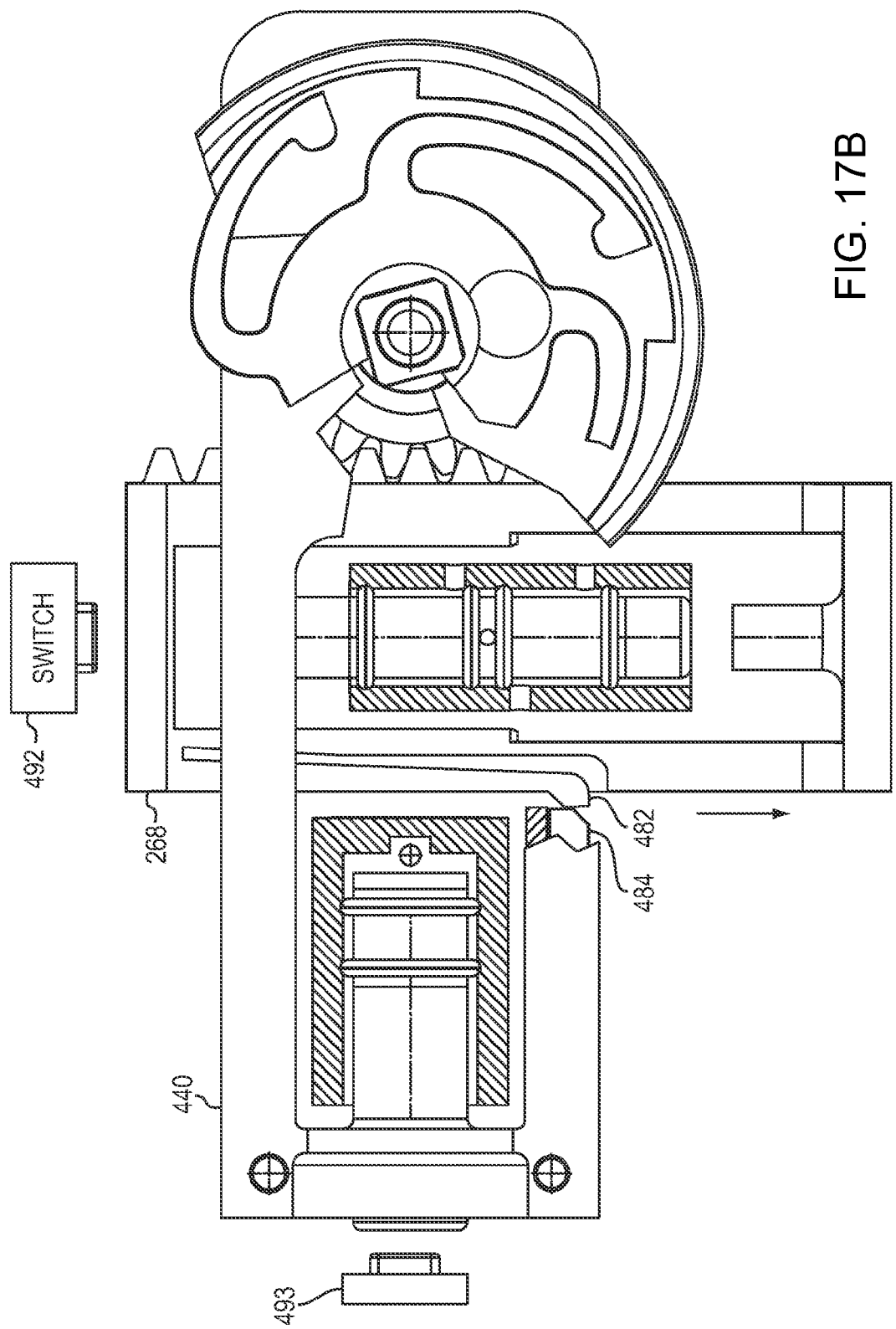

METHODS AND SYSTEMS FOR DOSING A
MEDICAMENT

FIELD OF THE INVENTION

This invention relates generally to medicament delivery devices and, more specifically, to systems and methods for delivering a single bolus dose when activated by a user.

BACKGROUND

Medicament infusion devices are utilized to deliver liquid fluid medicine to patients. For example, insulin infusion devices are often used by persons with diabetes to maintain adequate insulin levels throughout the day or to increase insulin levels during mealtime. These insulin infusion devices can replace the syringe-based injections common among those with diabetes.

Insulin infusion devices are available in several forms and include several common components. Generally, an infusion device includes a housing that may be worn on a patient's clothing (a belt, for example) or on the patient himself, and that contains a number of mechanical and electrical components. A reservoir holds the insulin and an electro-mechanical pump mechanism (various types are used) delivers the insulin as needed to the patient. Battery-powered electronics control the pump and ensure that the device is operating properly. Various sensors communicate with the electronics and other components to detect occlusions, sound alarms, measure remaining insulin capacity, etc.

While these devices are useful, they do suffer from several shortcomings. First, the high expense of the devices makes them accessible to fewer people than the diabetic population members who may benefit from their use. Second, failure or malfunction of one component requires repair or replacement of the entire device, a costly scenario. For example, if the pump fails, often the entire unit (including the properly functioning—and expensive—electronics) must be replaced. Third, over time the device gets dirty due to repeated uses, which requires periodic cleaning and may cause a failure condition at a later date. Fourth, the complexity of the devices requires significant battery power to operate pumps, monitor sensors, and send alerts and notifications to a patient. Power and electronic requirements are often so significant as to require large batteries, thus increasing the physical size, weight, and cost of the device. Fifth, in devices which administer a liquid fluid medicine on demand, a full dose may not always be delivered.

It is therefore desirable to ensure the delivery of a single, full dose of medicament with a low-cost, mechanical mechanism in a reliable and safe manner.

SUMMARY OF THE INVENTION

In one aspect, the invention relates to a method of dosing a medicament using a mechanical pump system including an actuation element, a direct drive piston system including a piston, and a lost motion valve system. The method includes the steps of moving the actuation element from a rest position to a fill end position to fill incrementally a piston chamber of the piston system with medicament from a reservoir, moving the actuation element an additional distance to a point of no return to move a valve of the valve system from a fill position to a dosing position, and moving the actuation element past the point of no return to force a full dose of medicament out of the piston chamber to a dosing conduit.

In one embodiment of the above aspect, moving the actuation element from the rest position to the fill end position retracts the piston relative to the piston chamber. In another embodiment, the direct drive piston system includes a rack and gear system or a cam and follower system. The direct drive piston system may include both the rack and gear system and the cam and follower system. In another embodiment, moving the actuation element from the rest position to the fill end position does not move the valve. In yet another embodiment, when the actuation element is moved past the point of no return, the piston is decoupled from the actuation element and automatically delivers a full dose of medicament to the dosing conduit.

In another embodiment of the above aspect, the method includes returning the actuation element to the rest position after dosing to reset the mechanical pump system. The actuation element may be returned to the rest position automatically and may pass through a reengagement position prior to reaching the rest position. In one embodiment, cycling the actuation element from past the point of no return to a position intermediate with the reengagement position delivers no additional medicament. In another embodiment, cycling the actuation element between the rest position and a position before the point of no return delivers no medicament. The actuation element may exert a first increasing reaction force against an actuating force when filling the piston chamber to the fill end position and a second lower reaction force when the actuation element moves past the fill end position.

In yet another embodiment of the above aspect, the valve may be moved from the dosing position to the fill position by the actuation element. The valve may allow fluidic communication between the reservoir and the piston chamber only when the valve is in the fill position, and the valve may allow fluidic communication between the piston chamber and the dosing conduit only when the valve is in the dosing position. The piston system and the valve system may be configured to preclude direct fluidic communication from the reservoir to the dosing conduit. The reservoir may hold a first volume of medicament less than a volume of a replenishment reservoir. In further embodiments, the valve system includes a redundant sealing system having two sealing elements disposed between the reservoir and the dosing conduit and a venting port disposed between the two sealing elements for dumping medicament leaked between the two sealing elements. The piston system and the valve system may preclude delivery of a partial dose of medicament to the dosing conduit. The mechanical pump system may also include an interlock for retaining the valve in the dosing position until a full dose of medicament is delivered.

In another embodiment of the above aspect, the method includes delivering a signal only when the full dose is delivered to the dosing circuit. The signal may be triggered by a mechanical, an optical, a capacitive, a potentiometric, or a magnetic input. The signal may be triggered based on detecting a specific position, a change in position, a threshold velocity, or a change in velocity of a moving component of the mechanical pump system. The signal may be a tactile stimulus, an audible stimulus, a visual stimulus, an electronically detectable signal adapted to be received by an electronic device, or combinations thereof.

In another aspect, the invention relates to a mechanical pump system including an actuation element and a direct drive piston system including a piston chamber, a piston disposed within the piston chamber, and a direct drive coupled to the actuation element for moving the piston relative to the piston chamber when the actuation element moves from a rest position to a fill end position to fill incrementally the piston chamber with medicament. The mechanical pump system also includes a lost motion valve system including a valve chamber and a valve disposed within the valve chamber. The valve is displaced from a fill position to a dosing position after the actuation element travels beyond the fill end position.

In one embodiment of the above aspect, the actuation element is a manually operable button. The actuation element may form a gap with the valve so the valve does not move when the actuation element moves from the rest position to the fill end position. The actuation element may contact the valve when the actuation element is beyond the fill end position. In another embodiment, the mechanical pump includes a return spring for biasing the actuation element toward the rest position. The piston chamber may contain a full dose of medicament when the actuation element is at the fill end position to preclude delivery of a partial dose of medicament to a dosing conduit. The mechanical pump system may include an interlock for retaining the valve in the dosing position until a full dose of medicament is delivered. Moving the actuation element from the rest position to the fill end position may compress a piston spring and an actuation element return spring, resulting in a first increasing reaction force, and moving the actuation element past the fill end position toward the point of no return compresses further solely the return spring. The piston spring may be substantially fully reacted by a cam disk when the actuation element reaches a point beyond the fill end position, resulting in a decrease in force required to move the actuation element toward the point of no return.

In another embodiment of the above aspect, the direct drive includes a rack and gear system or a cam and follower system. The direct drive may include both the rack and gear system and the cam and follower system. The cam and follower system may include a cam disk with a track for constraining motion of a piston bar coupled to the piston. The track may include a point corresponding to a point of no return of the actuation element beyond which the piston becomes decoupled from the actuation element. In yet another embodiment, the direct drive includes a ratchet element mating with the cam disk to decouple the actuation element from the piston. The mechanical pump system may include a piston spring for biasing the piston to empty the piston chamber when the piston is decoupled from the actuation element. The cam disk may include a ledge for mating with the ratchet element to recouple the actuation element to the piston at a reengagement position. In other embodiments, the ratchet element and the cam disk may be configured so that cycling of the actuation element from past the point of no return to a position intermediate with the reengagement position fails to deliver medicament through the valve, and the actuation element and the cam disk may be configured so that cycling of the actuation element between the rest position and a position before the point of no return delivers no medicament.

In yet another embodiment of the above aspect, the valve fluidically couples a reservoir and the piston chamber only when the valve is in the fill position. The reservoir may hold a first volume of medicament less than a volume of a replenishment reservoir. The valve may fluidically couple the piston chamber and a dosing conduit only when the valve is in the dosing position and the valve system may preclude direct fluidic communication between a reservoir and a dosing conduit. The valve system may include a fluidic outlet for dumping medicament if pressure exceeds a predetermined limit.

In one embodiment of the above aspect, the mechanical pump system includes a signaling device for delivering a signal as a full dose of medicament is delivered. The signaling device may be triggered by a mechanical, an optical, a capacitive, a potentiometric, or a magnetic input. The signaling device may be triggered when a specific position, a change in position, a threshold velocity, or a change in velocity of a moving component of the mechanical pump system is detected. The signaling device may provide a tactile stimulus, an audible stimulus, a visual stimulus, an electronically detectable signal adapted to be received by an electronic device, or combinations thereof.

BRIEF DESCRIPTION OF THE FIGURES

Other features and advantages of the present invention, as well as the invention itself, can be more fully understood from the following description of the various embodiments, when read together with the accompanying drawings, in which:

FIG. 6 is a schematic exploded view of the mechanical pump system depicted in

FIG. 5, in accordance with one embodiment of the invention;

FIG. 15A1 is a schematic partial plan view of a mechanical pump system with an actuation button approaching a point of no return and an interlock, in accordance with one embodiment of the invention;

FIG. 15A2 is a schematic partial cutaway view of a cam disk of the mechanical pump system depicted in FIG. 15A1 approaching the point of no return;

FIG. 16A1 is a schematic partial plan view of a mechanical pump system with an actuation button past the point of no return and an interlock, in accordance with one embodiment of the invention;

FIG. 16A2 is a schematic partial cutaway view of a cam disk of the mechanical pump system depicted in FIG. 16A1 past the point of no return;

FIG. 17B is a schematic partial plan view of the mechanical pump system of FIG. 17A after delivering a dose and returning the actuation button to a rest position;

DETAILED DESCRIPTION

Figure 1:
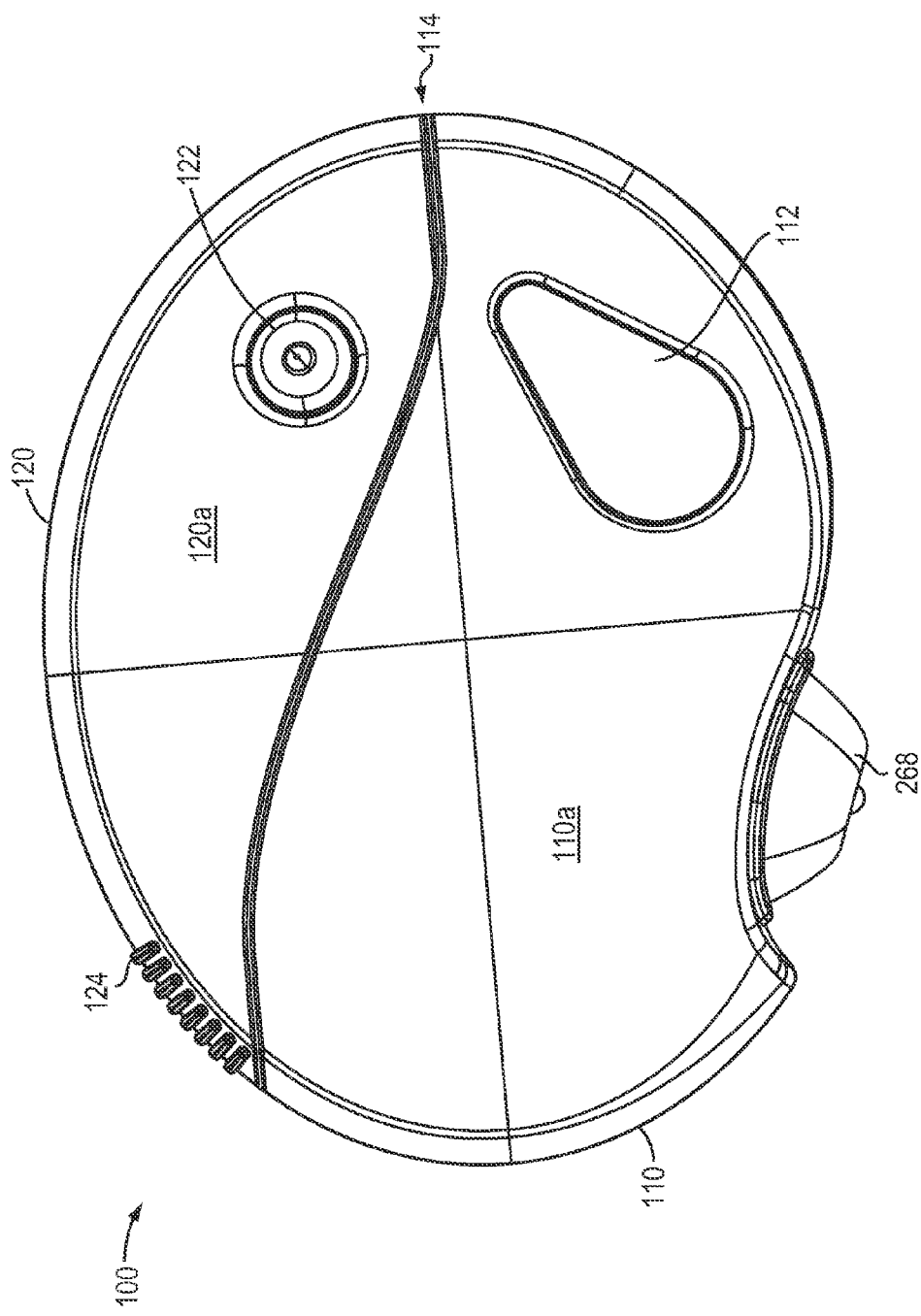
FIG. 1 is a schematic top view of a fluid medicament delivery device in accordance with one embodiment of the invention.
Figure 2:
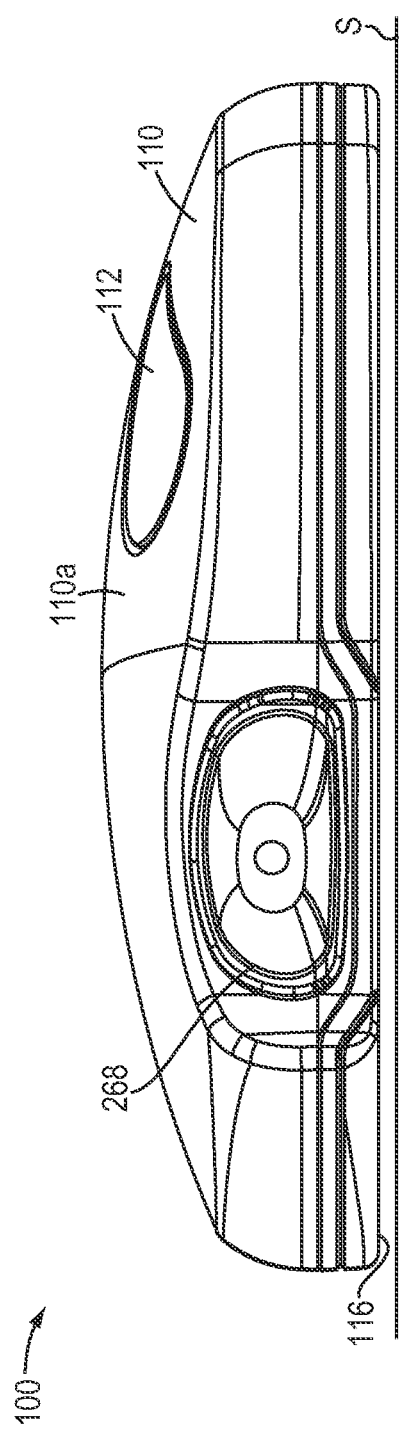
FIG. 2 is a schematic side view of the fluid medicament delivery device of FIG. 1.

FIGS. 1 and 2 depict an embodiment of an assembled fluid medicament delivery device 100 having at least two modules, a patient attachment unit 110 and a separate indicator unit 120, each having a housing 110a, 120a, respectively. As will readily be appreciated, the invention is not limited in this respect, but is being presented in this two module device for purposes of explanation only. For additional detail on this type of system see, for example, U.S. patent application Ser. No. 12/542,808, filed Aug. 18, 2009, the disclosure of which is hereby incorporated by reference herein in its entirety. The invention has applications across a wide variety of fluidic medicament delivery devices. The depicted fluid medicament delivery device 100, when assembled, defines a substantially oval shape, although other shapes (circular, oblong, elliptical, etc.) are also contemplated. In general, an assembled device having round corners, smooth edges, etc., may be desirable, since the device is designed to be worn on the skin of a patient, underneath clothing. Other aspects of the device that make it generally unobtrusive during wear include a small size (only about several inches across) and a low profile. Other device shapes and sizes are also contemplated.

The patient attachment unit 110 includes a bolus button (or actuation element) 268 for delivering a dose of fluid medicament, as described below. A cannula insertion device is used to insert a cannula through the device 110, subcutaneously through the skin S of a patient. Cannula insertion devices are described in U.S. Pat. No. 7,846,132, issued Dec. 7, 2010, the disclosure of which is hereby incorporated by reference herein in its entirety. After insertion, the cannula insertion device is disconnected from the patient attachment unit 110, and a cap 112 is used to seal the opening to prevent ingress of contaminants, moisture, etc. The separate indicator unit 120 includes an indicator button 122. A textured edge 124, may be present along all or part of the edge of the housing 120a to provide a gripping surface during attachment and/or disconnection of the indicator unit 120 from the patient attachment unit 110. Alternatively or additionally, the edge of patient attachment unit housing 110a may also be textured.

The patient attachment unit 110 is connected to and in communication with the separate indicator unit 120. The housings 110a, 120b of the patient attachment unit 110 and the indicator unit 120 meet at a curved interface 114. Interfaces having other mating shapes are also contemplated. The bottom surface of the patient attachment unit 110 includes a patient attachment interface 116. The patient attachment interface 116 may include one or more adhesive pads secured to the bottom surface of the patient attachment unit 110 for adhering the fluid medicament delivery device 100 to the skin S of a patient during use. The interface 116 may be any suitable configuration to adhere reliably the patient attachment unit 110 to the skin S. In one embodiment, the interface 116 includes a plurality of discrete points of attachment. Other embodiments utilize concentric adhesive circles or ovals.

The indicator button 122 may be used by the patient to test the functioning of the fluid medicament delivery device 100, to cancel a notification presently being delivered, or to prompt for a repetition of a previous message or other information stored by the indicator unit. Actuating the indicator button 122 may initiate one or more tests to indicate to the patient various operational or therapy states of the device 100, such as whether the separate indicator unit 120 is properly mounted to the patient attachment unit 110, whether an internal battery has sufficient power for continued use, and/or whether pressure sensing within the device 110 is operating properly. Other tests are also contemplated. A single indicator button 122 may be used to run one or more tests. The medicament delivery device 100 may be programmed to recognize patterns of actuations of the indicator button to initiate certain test routines. That is, two actuations in quick succession may initiate a "Battery Power Available" test routine, three actuations in quick succession may initiate a "Pressure Sensor Check" test routine, etc. Other combinations of short actuations and long actuations (e.g., Short, Long, Short; Long, Long, Short, etc.) are also contemplated to initiate any number of test routines. Alternatively or additionally, two or more buttons or other input features may be included on the device, for initiating one or more separate tests. Positive or negative feedback of the test results may be provided to the patient in the form of audible sounds of differing tones or durations, illumination/delumination of lights, vibrations, and combinations thereof. In certain embodiments, light emitting diodes (LEDs) may be used to illuminate the button itself or may illuminate portions of the indicator unit housing to provide feedback to the patient. Graphical indicia or alphanumeric information may be displayed on a suitable output device.

Figure 3:
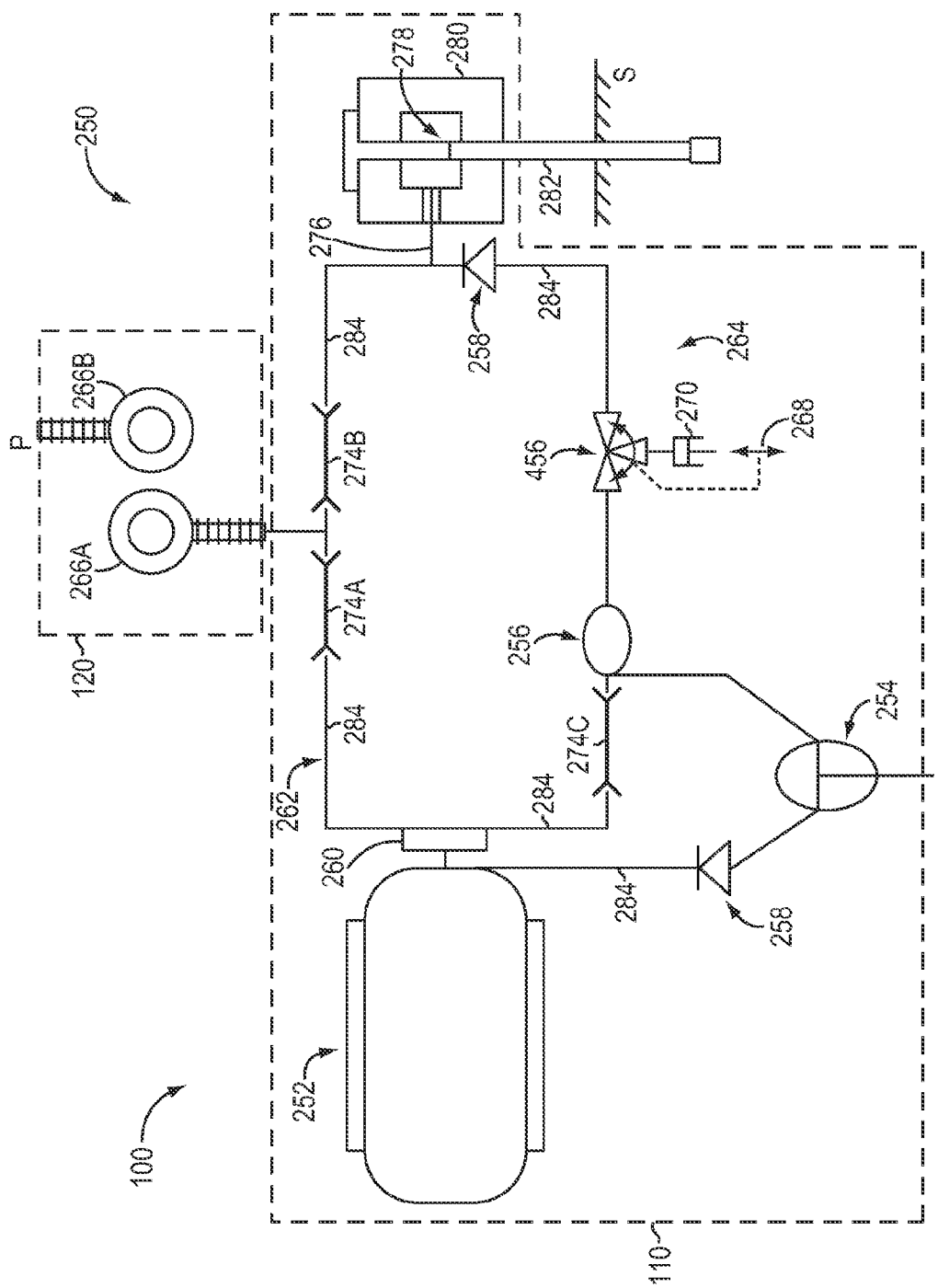
FIG. 3 is a schematic diagram of an exemplary infusion device micro-fluidic circuit in accordance with one embodiment of the invention.

FIG. 3 is a schematic diagram of an exemplary infusion device micro-fluidic circuit 250 that may be incorporated into the fluid medicament delivery device 100 described herein. Other infusion devices having micro-fluidic circuits are described in U.S. Pat. No. 7,517,335, issued Apr. 14, 2009, the disclosure of which is hereby incorporated by reference herein in its entirety. The micro-fluidic circuit 250 includes a pressurized or replenishment reservoir 252 that is, in this case, an elastomer bladder. Alternatively, a flexible vessel or bag compressed by a spring or external pressure or force may be utilized. A fill port 254 is used to introduce fluid, such as insulin, to the micro-fluidic circuit 250. In this micro-fluidic circuit 250, introducing insulin via the fill port 254 fills both the reservoir 252 and a variable-volume bolus reservoir 256. Check valves 258 prevent backflow of insulin in a number of locations.

During use, insulin is forced from the reservoir 252 by elastic contraction of the elastomer, through a filter 260, and into two parallel flowpaths, a basal flowpath 262 and a bolus flowpath 264. The basal flowpath 262 delivers a constant dose or steady-state level of insulin to a patient; the bolus flowpath 264 delivers a bolus dose of insulin to the patient as needed or desired by the patient, for example, in conjunction with a meal. The basal flowpath 262 includes a first pressure sensor 266A or other pressure or flow sensors in communication with the flowpath 262, for example, at a mid-point in the basal flowpath. In an alternative embodiment, the first pressure sensor 266A or first sensing element may be placed further upstream or downstream in the basal flowpath, as desired. In another alternative embodiment, a plurality of pressure sensors in communication with the basal flowpath 262 may be utilized. A second pressure sensor 266B or second sensing element is exposed to ambient air pressure P. The function of and relationship between the pressure sensors 266A, 266B is described in more detail in the patent application referred to above (i.e. U.S. patent application Ser. No. 12/542,808). In one embodiment, the pressure sensors 266A, 266B consist of micro-electronic-mechanical system (MEMS) sensors. Each MEMS sensor is about 2 mm square, but sensors having different dimensions may also be used. Both MEMS sensors are contained within the indicator unit 120. In FIG. 3, the pressure sensor 266A communicates with a portion of the basal circuit 262 between two flow restrictors 274A, 274B (e.g., microcapillaries). In one embodiment, this portion between the flow restrictors 274A, 274B may be a pressure sensor chamber. The pressure sensor 266A senses pressure changes in the basal flowpath 262, which may be indicative of occlusion conditions that increase pressure therein. The pressure sensor 266B senses changes in ambient air pressure external to the fluid medicament delivery device 100. The pressure sensors 266A, 266B are absolute pressure sensors, but a single relative pressure sensor may also be utilized. A relative pressure sensor, e.g., a gauge MEMS sensor, may be used to replace both absolute pressure sensors.

To deliver a bolus via the bolus flowpath 264, the patient presses a button (or other actuation element) 268 that drives a single stroke of a bolus piston 420 in a displacement or piston chamber 270 and moves a 3-way slide valve 456 to deliver a single bolus dose. The valve 456 is configured to provide a redundant sealing system for safety purposes, as described in greater detail below. An optional flow restrictor 274C regulates, in part, the fluid flow through the bolus flowpath 264. The parallel flowpaths 262, 264 join at a common channel or dosing conduit 276 upstream of an internal chamber or a cannula void 278. The cannula void 278 is formed in a cannula base 280, which allows a point of connection to a cannula 282. The cannula 282 extends below the skin S of a patient, thus delivering the insulin subcutaneously. In one embodiment, the actuation of the bolus button 268 may be sensed by the indicator unit 120 with, for example, a magnetic sensor, a Hall effect sensor, or a switch. In an alternative embodiment of the present invention, at least one pressure sensor may be placed in the bolus flowpath 264, thereby allowing the indicator unit 120 to sense the actuation of the bolus button 268. Other alternative sensing and signaling embodiments are discussed below. Conduits 284 having diameters larger than those of the flow restrictors 274A, 274B, 274C connect the various components, generally in serial flow relation.

Figure 4:
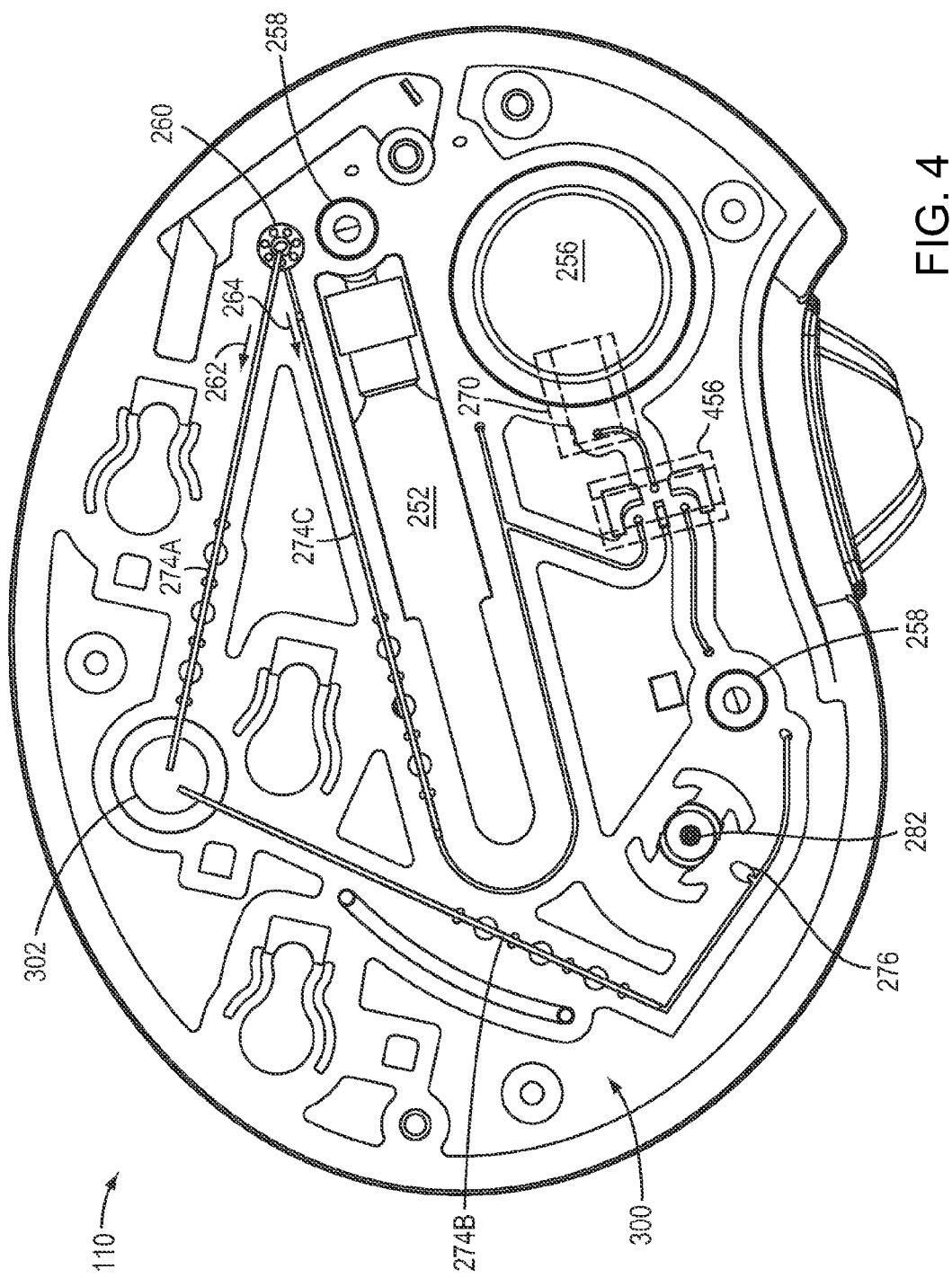
FIG. 4 is a schematic bottom view of a patient attachment unit of the fluid medicament delivery device of FIG. 1 with an external housing removed.

FIG. 4 depicts a bottom view of the patient attachment unit 110 showing the internal components and structures therein, with the housing removed. Specifically, the bottom portion of the housing 110a, to which the attachment interface 116 is secured, has been removed. These internal components and structures correspond generally to the micro-fluidic circuit 250 discussed in FIG. 3. The components and structures in the patient attachment unit 110 may be disposed in or connected to a flow manifold 300, which serves as a mounting platform for the various components. Note that not all conduits and flow components are depicted in FIG. 4, as some components may be secured to the opposite side of the manifold 300 or formed therein.

As described above with regard to FIG. 3, insulin in the bolus flowpath 264 (the bolus flowpath 264, in FIG. 4, is downstream of the labeled arrow) of the micro-fluidic circuit 250 is delivered from the elastomer reservoir 252, filtered through the filter 260, and stored in the variable-volume bolus reservoir 256. In certain embodiments, the elastomer reservoir 252 may have a total volume of about 3200 microliters. The variable-volume bolus reservoir 256 may have a total volume of about 180 microliters to about 260 microliters. Other volumes of the various components are also contemplated. When the fluid pressure in the elastomer reservoir 252 is greater than the fluid pressure in the variable-volume reservoir 256, the variable-volume reservoir 256 will continue to fill, subject to the flow rate dictated at least by flow restrictor 274C in the bolus flowpath 264. Downstream of the variable-volume bolus reservoir 256 is the bolus displacement piston chamber 270, which may store a single dose of insulin (e.g., about 5, about 10, about 20, about 25, or greater than about 25 microliters of insulin, in various embodiments).

Actuating the bolus button 268 shifts the valve 456 (See FIG. 3) to fluidically couple the piston chamber 270 with the dosing conduit 276 and empties the entire contents of the bolus displacement piston chamber 270, as described in greater detail below. A check valve 258 allows for free flow of insulin from the valve 456 to the dosing conduit 276. The check valve 258 prevents backflow during a bolus stroke (i.e., actuation of the bolus button 268) to deliver the single bolus dose. Audible, visual, and/or tactile feedback may be provided to the patient to signal that a bolus has been delivered. Releasing the bolus button 268 resets the valve 456 to fluidically couple the piston chamber 270 to the variable-volume bolus reservoir 256. The displacement piston chamber 270 is then refilled with insulin from the variable-volume bolus reservoir 256, which is, in turn, filled with insulin from the reservoir 252. The bolus flow rate is controlled with a fixed volume-per-stroke of bolus stimulus, i.e., a predetermined volume of insulin-per-stroke. In another embodiment, the bolus flow control rate also may be controlled by a bolus rate flow restrictor. Also, downstream of the filter 260 is the basal flowpath 262 (the basal flowpath 262, in FIG. 4, is downstream of the labeled arrow) of the micro-fluidic circuit 250. The flow restrictors 274A, 274B are located on opposite sides of a pressure sensor chamber 302.

In various embodiments, each flow restrictor 274A, 274B has a length in a range of about 18 mm to about 35 mm. Other lengths of the flow restrictors are also contemplated, for example, from about 10 mm to about 20 mm. The various channels 284 in the manifold 300 may be formed by, for example, laser cutting, and the flow restrictors 274A, 274B may be placed therein. The flow restrictors 274A, 274B may be glued or fused into the channels, though other methods of retention are also contemplated. Exemplary flow restrictors are described in U.S. Pat. No. 7,520,295, issued Apr. 21, 2009, the disclosure of which is hereby incorporated by reference herein in its entirety. The flow restrictors 274A, 274B are connected to and in fluidic communication with a pressure sensor chamber 302.

Figure 5:
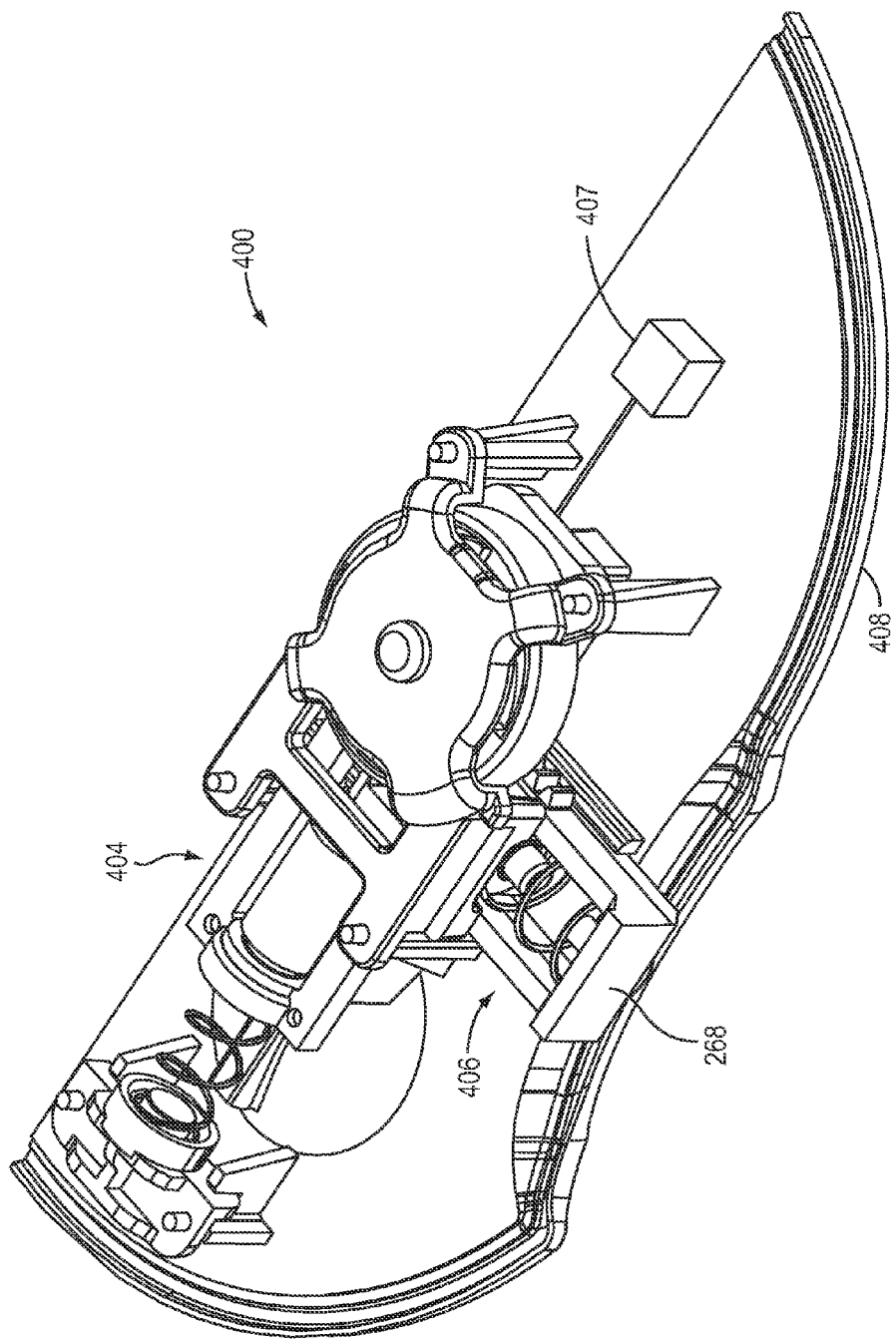
FIG. 5 is a schematic perspective view of a mechanical pump system in accordance with one embodiment of the invention.

In order to ensure safe reliable operation and prevent delivery of partial doses, in one particular embodiment of the bolus circuit, a manually driven mechanical pump system 400 is used, as depicted in FIG. 5. The mechanical pump system 400 includes the bolus button actuation element 268, a direct drive piston system 404, and a lost motion valve system 406. The mechanical pump system 400 may also include a signaling device, shown schematically at 407, and may be mounted on a base 408.

Figure 6:
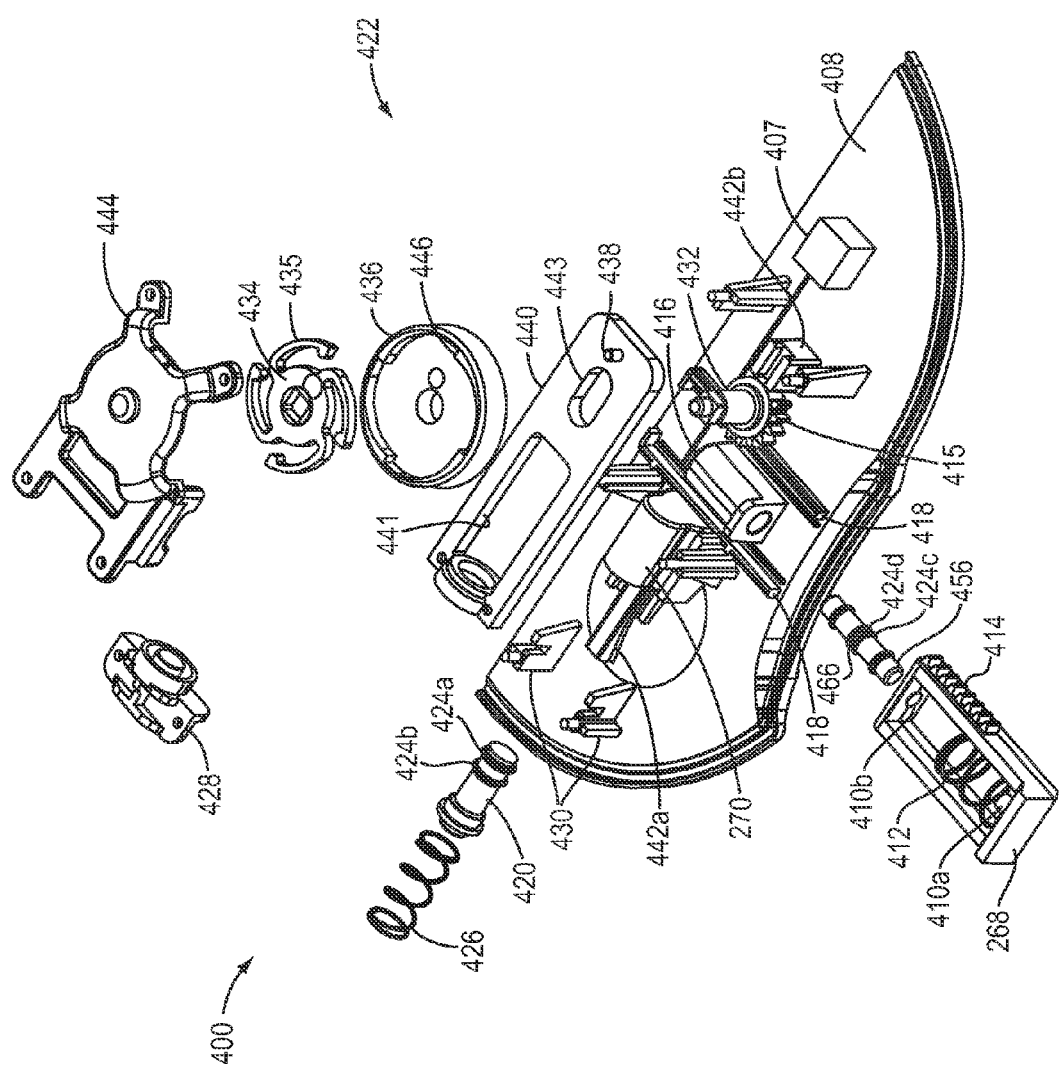

FIG. 6 depicts the mechanical pump system 400 of FIG. 5 in an exploded view. In one embodiment, the actuation element 268 is substantially rectangular with a hollow interior. Alternate shapes are contemplated. An end surface of the actuation element 268 may be configured as a push button for simple manual operation. The actuation element 268 forms valve contacts 410a, 410b at opposite ends within the hollow interior. A return spring (or valve spring) 412 is disposed about the valve contact 410a. A rack 414 for mating with a pinion gear 415 (together forming a rack and pinion gear system) is disposed on an exterior side wall of the actuation element 268. When the mechanical pump system 400 is assembled, the actuation element 402 substantially surrounds a valve chamber 416 of the lost motion valve system 406 (described in greater detail below). The actuation element 268 is in sliding contact with the base 408 and may be guided by a pair of actuation element guides 418 or other suitable structure to ensure smooth, sliding action during manual actuation and spring return.

The direct drive piston system 404 includes the piston chamber 270, the piston 420, and a direct drive 422 for moving the piston 420. The piston chamber 270 is fluidically coupled to the valve chamber 416 via a piston chamber inlet/outlet 423 (shown in FIG. 8A). The piston chamber 270 is configured to slidably house the piston 420. One end of the piston chamber 270 may be substantially open to allow for a portion of the piston 420 to travel into and out of the piston chamber 270. The piston chamber 270 and the piston 420 may be substantially cylindrical, or any other complementary shape, which allows for slidable contact. The piston 420 has at least one seal to sealingly engage sidewalls of the piston chamber 270 so that fluid may not pass beyond the seal. The depicted embodiment has a pair of seals, 424a and 424b. A piston spring (or pump spring) 426 is coupled to the piston 420 and a piston retainer 428. The piston retainer 428 is in a fixed position, mounted on supports 430 on the base 408. As the piston retainer 428 is fixed, the piston spring 426 is configured to constantly bias the piston 420 into the piston chamber 270 to empty the chamber 270.

The direct drive 422 includes the rack 414 and the gear 415 (the rack and gear system), a drive shaft 432, a ratchet 434, a cam disk 436 and a follower 438 (a cam and follower system), a piston bar 440, and piston bar guides 442a, 442b. A support structure 444 may be provided to support the drive shaft 432 and provide smooth, reliable operation of the direct drive 422.

The pinion gear 415 is configured to mate with the rack 414, such that teeth on each are sized and positioned accordingly to allow for a predetermined range of piston travel. The gear 415 may be formed integrally with the drive shaft 432. The drive shaft 432 is mounted to the base 408, but allowed to rotate relative thereto. While the drive shaft 432 may be substantially round, an upper portion may be a polygonal shape, such as a square or a triangle, to securely engage a corresponding shape on the ratchet 434 to prevent slip. Because of this configuration, movement of the ratchet 434 is directly linked to movement of the actuation element 268 through the rack and gear system. The ratchet 434 may include four curved ratchet arms 435, each spaced equidistantly about a central circular perimeter and configured for engaging four ledges 446 of the cam disk 436. When configured in this manner, each full stroke actuation of the bolus button 268 causes a ninety degree rotation of the cam disk 436.

In one embodiment, the ratchet 434 mates with an upper surface of the cam disk 436. The upper surface of the cam disk 436 includes the four ledges 446, each configured for engagement with a respective ratchet arm 435 to allow for simultaneous engagement during clockwise rotation. However, the ratchet 434 does not drive movement of the cam disk 436 when the ratchet 434 is moved in a counter-clockwise direction, allowing each ratchet arm 435 to eventually reengage a different ledge 446. This process is described in greater detail below.

Figure 8A:
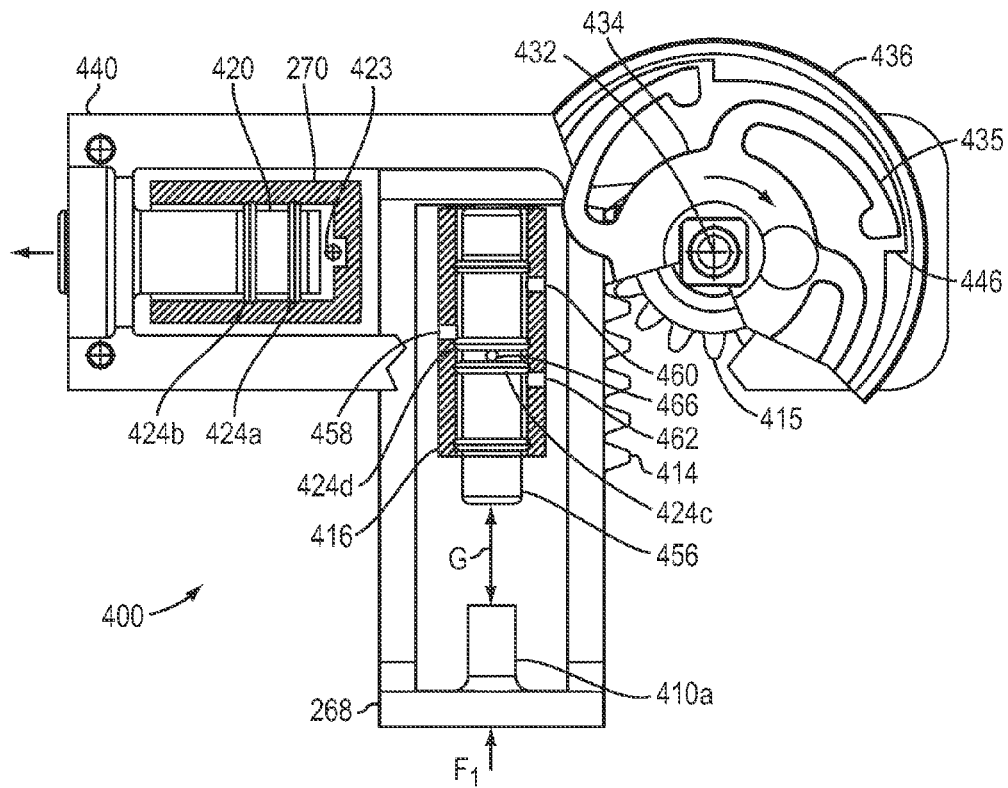
FIG. 8A is a schematic partial plan view of a mechanical pump system with an actuation button at a rest position, in accordance with one embodiment of the invention.
Figure 8B:
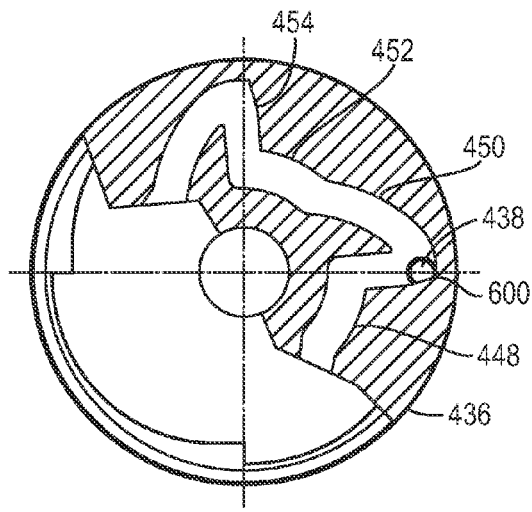
FIG. 8B is a schematic partial cutaway view of a cam disk of the mechanical pump system depicted in FIG. 8A at the rest position.

A bottom surface of the cam disk 436 may form a track 448, as depicted in FIG. 8B. The track 448 includes four identical sectors, each occupying a quarter of the bottom surface of the cam disk 436. Each segment includes three distinct sections: a first section of decreasing radius 450, a second section of substantially constant radius 452 (e.g., slightly decreasing radius), and a third section of steeply increasing radius 454. The track 448 is configured to slidingly interface with and drive the follower 438, which may be a pin formed integrally with or mounted to the piston bar 440. As the track 448 rotates, the pin 438 translates horizontally relative to the center of the cam disk 436. The pin 438 follows the track 448 and constrains the motion of the piston bar 440 to the rotation of the cam disk 436.

The piston bar 440 includes the pin 438 on one end and an opening 441 for straddling the piston chamber 270 and mating with the piston 420 at the opposite end. The piston bar 440 is dimensioned so that, for all points of travel, the seals 424a, 424b on the piston 420 remain within the piston chamber 270. The piston bar 440 may also form an opening (e.g., slot 443) so that the piston bar 440 substantially straddles the drive shaft 432. In one embodiment, the piston bar 440 is substantially rectangular, however any shape suitable for integrating with the other components may be used. The piston bar guides 442a, 442b are configured to provide smooth sliding surfaces for the piston bar 440, as well as to maintain the orientation of the piston bar 440.

Figure 14:
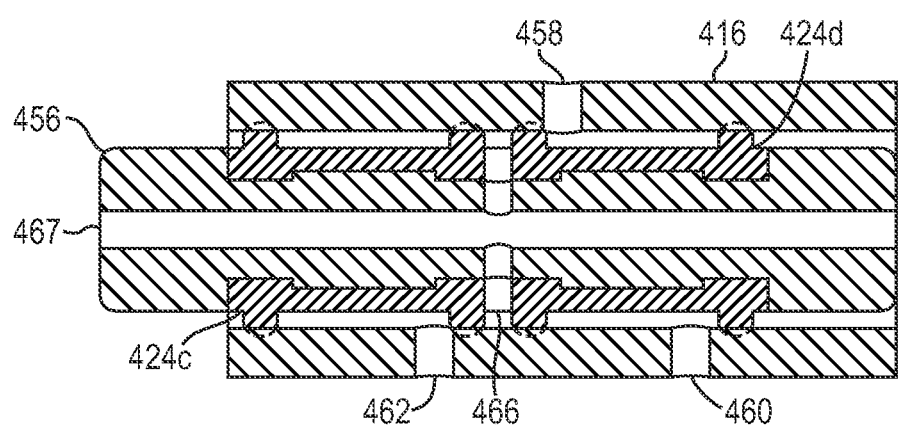
FIG. 14 is a schematic sectional view of a valve with a fluidic outlet of a mechanical pump system, in accordance with one embodiment of the invention.
Figure 15B:
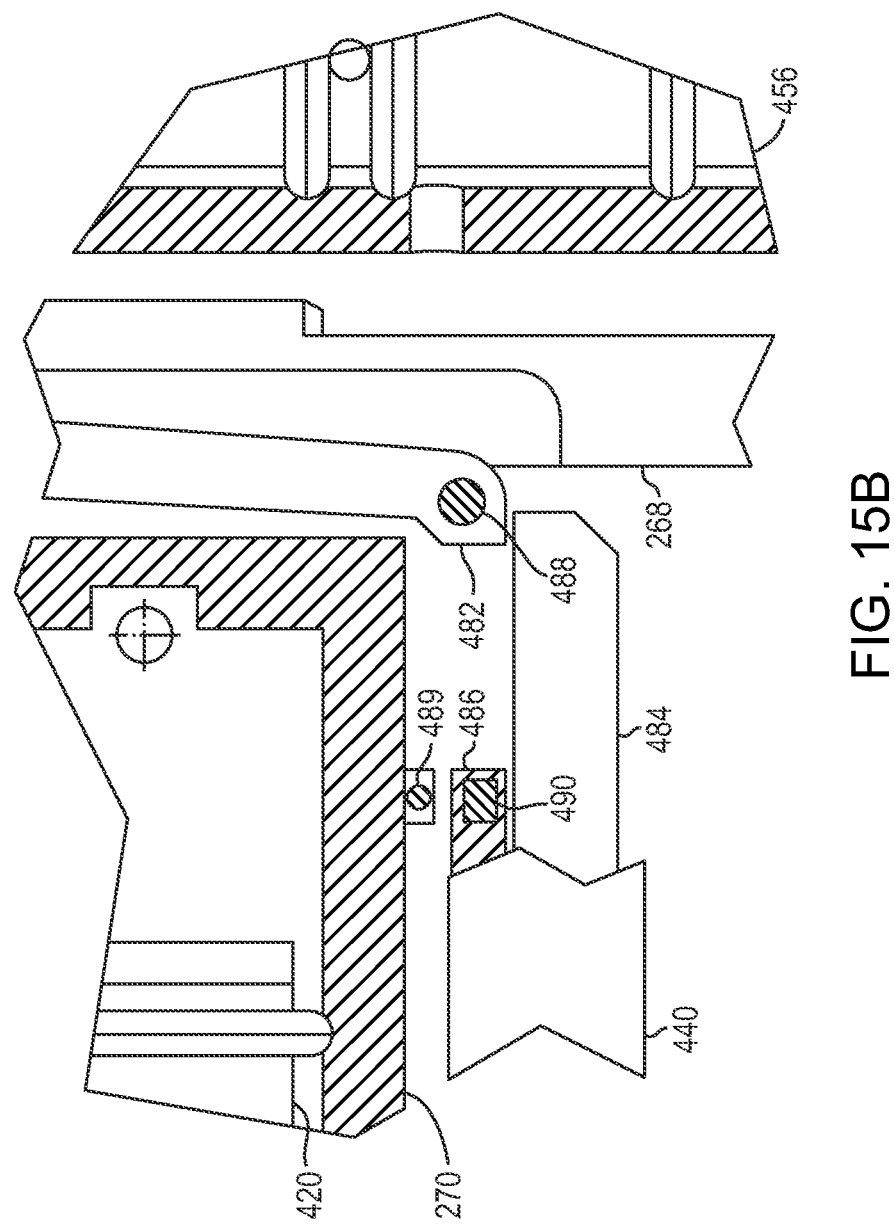
FIG. 15B is a schematic enlarged view of the interlock of the mechanical pump system depicted in FIG. 15A1.
Figure 16B:
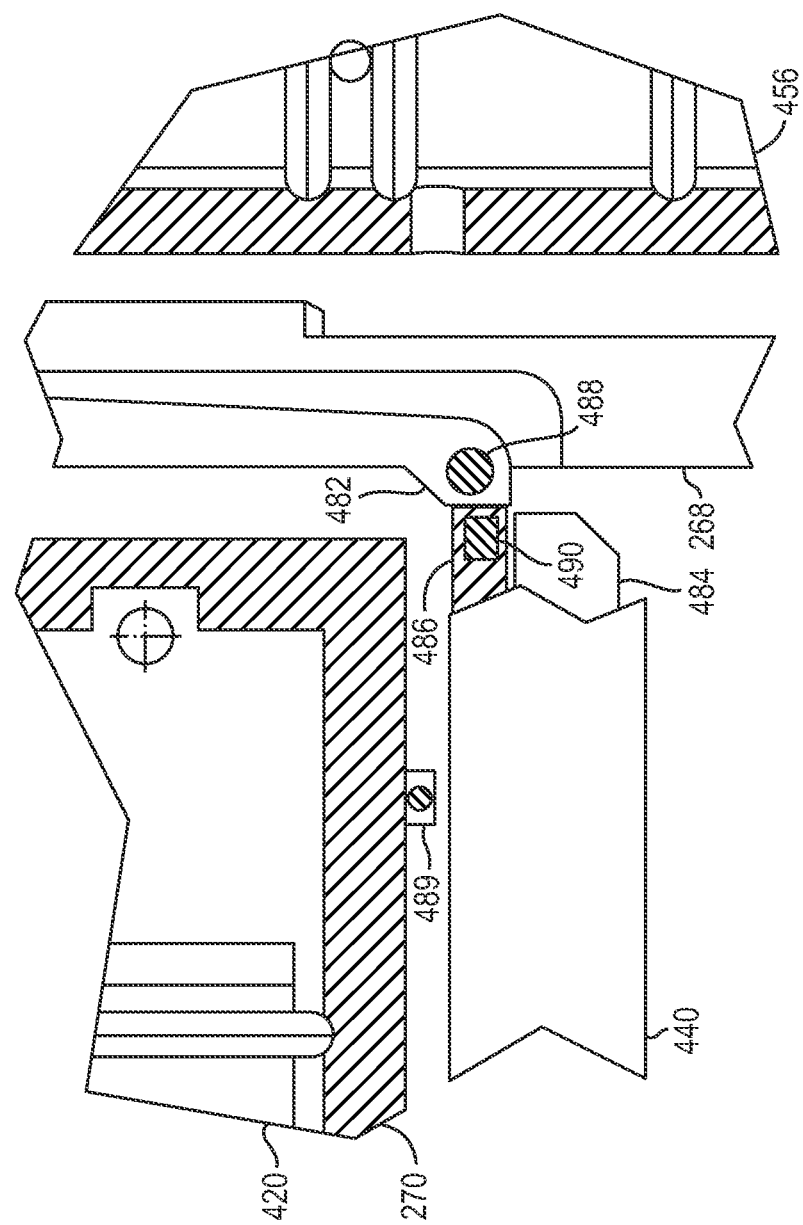
FIG. 16B is a schematic enlarged view of the interlock of the mechanical pump system depicted in FIG. 16A1.

The lost motion valve system 406 includes the valve chamber 416 and the valve 456 slidingly received therein. The valve chamber 416 is fluidically coupled to the piston chamber 270 via a valve chamber inlet/outlet 458, to the reservoir 256 via a reservoir inlet 460, and to the dosing conduit 276 via a dosing conduit outlet 462 (the inlets and outlets are best seen in FIG. 8A). The valve chamber 416 and the valve 456 may be cylindrical, or any other complementary shape which allows for slidable engagement. The valve 456 includes a pair of seals 424c, 424d, each located near a midpoint of the valve 456, to provide a redundant sealing system. Additional seals are also included near each end of the valve 456 to prevent fluid from leaking out of the valve chamber 416. The pair of seals 424c, 424d of the redundant sealing system are always disposed within the valve chamber 416 between the reservoir inlet 460 and the conduit outlet 462, due to the limited axial travel of the valve 456. The seals 424c, 424d provide a fluid-tight interface between the valve 456 and the valve chamber 416. This is a double fault condition to prevent leakage between the reservoir 256 and the dosing conduit 276 in the event of a single seal failure. A venting port 466 is optionally disposed between the seals 424 of the redundant sealing system for dumping any fluid which leaks into that zone due to a single or double seal failure (a triple fault condition). The fluid is dumped through a fluidic outlet 467 extending the length of the valve 456 with openings at either end that is connected with the venting port 466, rather than delivered to the dosing conduit 276 and ultimately the patient (See FIG. 14). This arrangement provides triple safety against leakage from the reservoir 256 to the patient, because such a connection may only be made after the failure of the two seals 424c, 424d and the venting port 466. This arrangement also provides safety against potential pressurized air bubbles in the piston chamber 270, since pressure is equilibrated to ambient when the valve 456 shifts from a fill position to a dosing position. As can be appreciated, these safety measures make this pump system 400 both safe and effective.

The signaling device 407 includes a link to a sensor or other element for indicating when a bolus dose has been delivered. Dosage delivery may be tracked to allow a user to confirm that the device delivered the medicament as intended. Undercounting deliveries may result in the user thinking a lesser amount of medication has been delivered, leading them to attempt to supply additional doses and creating a potentially dangerous overdosing situation. In each of the present embodiments, as described below, the signaling device 407 counts every dose delivered. A signal should correlate to actual dose delivery, and not be generated when a dose is not delivered, for example when the actuation element 268 is only partially depressed. In certain embodiments, getting an exact count may require tight mechanical tolerances. The sensor may sense any of a number of variables that may indicate when a dose has been delivered, such as pressure in the dosing conduit 276 or the position of the actuation element 268. The signaling device 407 may detect the specific position, the change in position, the threshold velocity, the change in velocity, or any other parameter of one of a number of elements that indicates a bolus dose has been or is about to be delivered, such as through a mechanical, an optical, a capacitive, a potentiometric, or a magnetic detection scheme. In another embodiment, the signaling device 407 may be triggered based on the detection of two different factors, such as the position of one element and the rate at which another element is travelling. For safety purposes, if there is any possibility of an inaccurate count, the signaling device 407 should preferably overcount, rather than undercount, to prevent a user from mistakenly delivering too many doses.

The signaling device 407 may provide a tactile stimulus, an audible stimulus, a visual stimulus, an electronically detectable signal adapted to be received by an electronic device, or any combination thereof to indicate to a user that a bolus dose has been delivered. The feedback may be active, such as an alarm or flashing light when the dose is delivered, or passive, such as a counter which detects the electronic signal and displays the number of doses. The dosage count may be stored in an electronic device and displayed later on demand in order to give the user or a caregiver the ability to study the dosing profile over a period of time (e.g., three days, a week, or longer). In some embodiments where a signal generating device, an electronic receiver, and an intelligent device (i.e., having an electronic circuit and software for decoding and interpreting signals to display a value, light, or some other indicia) for processing the signal are used, the signal generating device may be passive and placed in a low cost disposable subsystem, while the receiver and the intelligent device are placed in a reusable wall-to-wall electronic subsystem. The intelligent device may include an analog and/or digital electronic circuit to receive signals, decode signals, process signals, and display and/or store relevant data. A passive element (such as a magnet, a piece of magnetic material, a piece of high electrical permeability material, or an optical reflector) may be placed in the disposable device, while an electronic pick-up device (such as a coil, a GMR sensor, a reed relay, an inter-digitized capacitor, an optical switch or a regular electronic switch) may be placed in the reusable electronic subsystem. Preserving the most costly components in the reusable subsystem can reduce long term operational costs. Using a wireless signal may remove some obstacles for sending an electronic signal between water-proof subsystems (sometimes one disposable, one non-disposable), but the communicating devices should stay in communicable range during operation. Also, in some embodiments, the reusable electronic device may reduce its power consumption by spending much of its time in an ultra low-power mode (or deep sleep). A signal indicating delivery of a bolus dose may transmit sufficient energy to "wake-up" a micro-controller in the reusable device, such as approximately 2V, 1 μA for 1 μs or a minimum of approximately 2 pJ of energy.

Figure 7A:
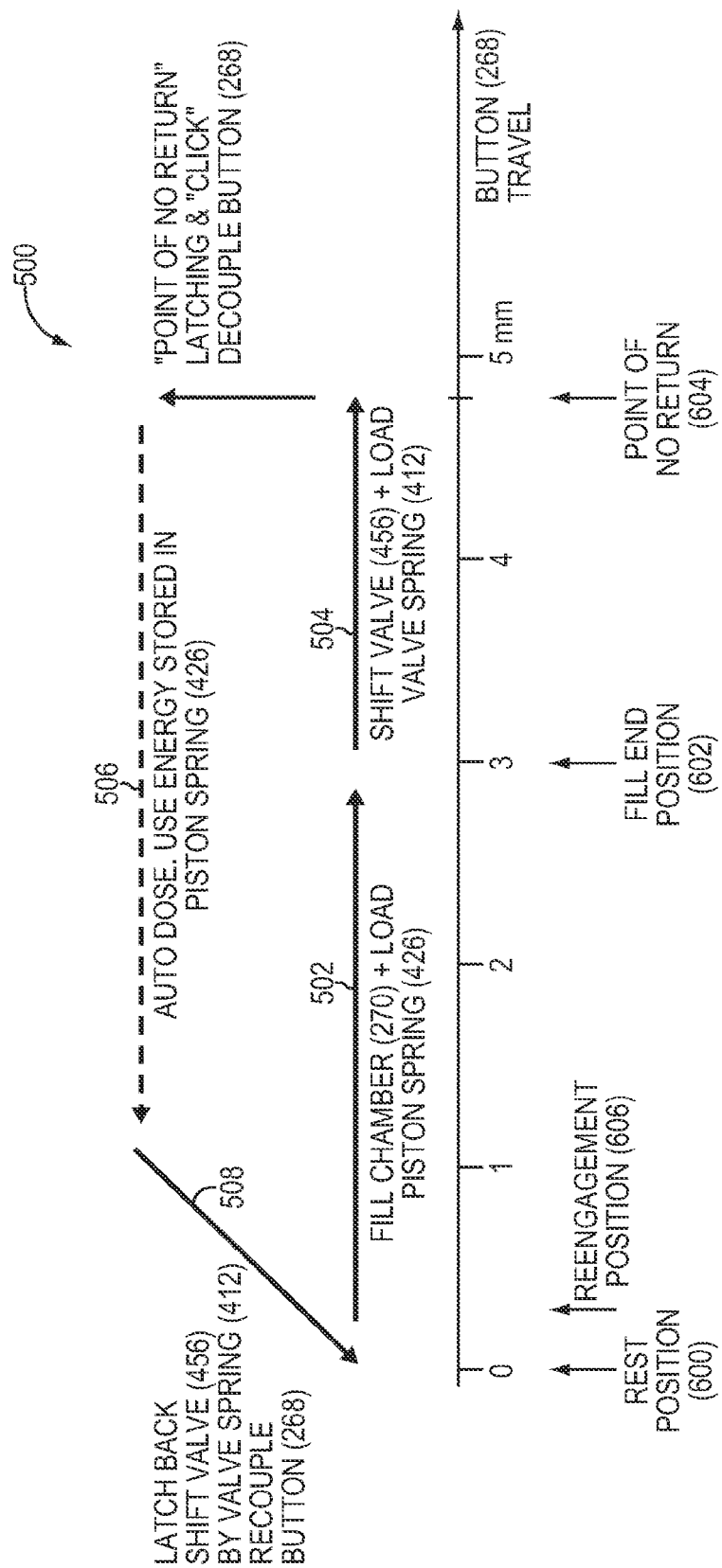
FIG. 7A is a schematic operational diagram of a mechanical pump system, in accordance with one embodiment of the invention.

FIG. 7A depicts schematically one method 500 of operating one embodiment of the mechanical pump system 400, relative to the travel of the bolus button 268. The method 500 includes a first step 502 of moving the actuation element or button 268 from a rest position 600 (i.e., at zero mm of button travel) to a fill end position 602 (i.e., at about three mm of button travel) to fill incrementally the piston chamber 270 with medicament from the reservoir 256, to load the piston spring 426 by retracting the piston 420 relative to the piston chamber 270, and to begin loading the valve spring 412. A second step 504 involves moving the actuation element 268 an additional distance beyond the fill end position 602 to a point just before a point of no return 604 to shift the valve 456 from a fill position to a dosing position and to fully load the valve spring 412. A third step 506 requires moving the actuation element 268 to an end of travel position just past the point of no return 604, to force a full dose of medicament out of the piston chamber 270 to the dosing conduit 276 by decoupling the actuation element 268 from the piston 420, thereby allowing the piston spring 426 to drive the piston 420 to empty the piston chamber 270. A fourth step 508 includes releasing the actuation element 268 to allow the actuation element 268 to move from the end of travel position to a reengagement position 606 to recouple the actuation element 268 to the piston 420 (i.e., by indexing of the ratchet 434 with the cam disk 436), and then to the rest position 600 to shift the valve 456 from the dosing position to the fill position, due to the action of the valve spring 412. This resets the mechanical pump system 400 to the state it was in at the start of the first step 502 permitting delivery of another full bolus dose, if desired. The mechanical operation of the mechanical pump system 400 during its operation 500 is described below in greater detail, with reference to FIGS. 8A-11B. Due to the unique arrangement and cooperation of the components, partial doses cannot be delivered, nor can there be direct fluidic communication between the bolus reservoir 256 and the dosing conduit 276 potentially resulting in an inadvertent overdosing condition.

Figure 7B:
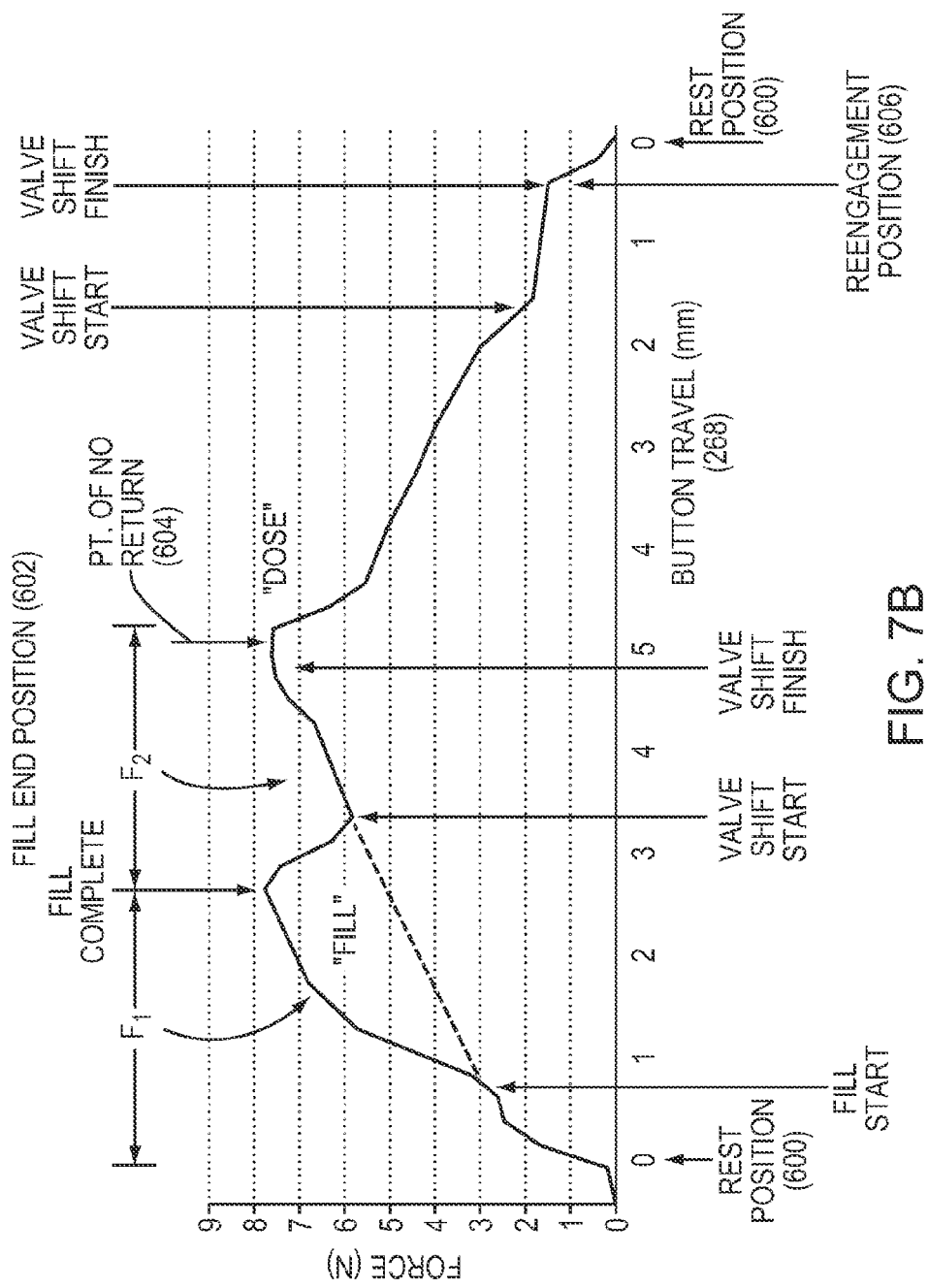
FIG. 7B is a graph schematically illustrating the actual measured reaction force experienced when operating a mechanical pump system with an actuation button through a complete dosing cycle, in accordance with one embodiment of the invention.

FIG. 7B depicts a graph schematically illustrating the actual measured reaction force experienced when moving the actuation element 268 through a complete dosing cycle of one embodiment of the device 100. The reaction force depends upon several variables, including the spring constants and range of compression of the piston spring 426 and the valve spring 412. The reaction force is also influenced by additional factors, such as frictional forces on the valve 456, the piston 420, and the follower 438, and a varying contact angle between the follower 438 and the track 448. Fluidic forces and seal stiction may also come into play. These additional factors affect some of the nuances of the force profile, though its primary shape is dictated by the reaction forces provided by the piston spring 426 and the valve spring 412. In this embodiment, the piston spring 426 has a greater spring constant than the valve spring 412 (the valve spring constant is displayed generally as the slope of the dashed line). Specific values for the reaction force along the vertical axis are dependent upon the respective spring constants and other system frictional losses. The numbers along the horizontal axis representing the position of the actuation element 268 are merely exemplary of one embodiment of the invention.

As the actuation element 268 is moved by the user from the rest position 600 to the fill end position 602, a required first actuating force $F_1$ increases generally linearly at a relatively high slope against a first reaction force, which is roughly a combination of the forces generated by compression of the piston spring 426 and the valve spring 412. The first reaction force peaks at the fill end position 602. As the actuation element 268 moves past the fill end position 602, the piston spring 426 is maintained in a fixed compressed position by the cam disk 436. Further travel of the actuation element 268 is compressing further solely the valve spring 412 and also moving the valve 456 from the fill position to the dosing position. This results in a dip or drop in the force profile, followed by a second lower magnitude and lower sloped reaction force provided solely by the partially compressed valve spring 412 and shifting of the valve 456. Accordingly, applying a second actuating force $F_2$ to move the actuation element 268 from the fill end position 602 to the end of travel position further compresses only the valve spring 412, resulting in a generally shallower slope. The second reaction force peaks at the end of travel position of the actuation element 268, where the valve spring 412 is close to its fully compressed or solid height. In one embodiment, the peak second reaction force, $F_2$, is less than the peak first reaction force, $F_1$.

The actuation distance between the fill end position 602 and the point of no return 604 is typically maintained sufficiently small, and the peak force $F_1$ is maintained sufficiently large that a user would be unable to react quickly enough to move the actuation element 268 past the fill end position 602 and yet reduce the actuation force enough to prevent the actuation element 268 from moving past the point of no return 604. Therefore, a user that moves the actuation element 268 past the fill end position 602 will reliably and inevitably also push the actuation element 268 past the point of no return 604 to deliver a full dose of medicament. The greater the difference between the higher peak first reaction force $F_1$ and the lower peak second reaction force $F_2$, and the lesser the actuation distance between the peak forces, the more inevitable it becomes that the user necessarily moves the actuation element 268 past the point of no return 604.

FIGS. 8A and 8B depict the mechanical pump system 400 at the start of the first step 500. The actuation element 268 is in the rest position 600 (shown in FIG. 7) and the valve 456 is in the fill position. A gap G exists between the valve contact 410a and the valve 456. This gap allows for the actuation element 268 to move to the fill end position 602 to withdraw the piston 420 and fill the chamber 270 with a full dose before moving the valve 456. The bolus reservoir 256 and the piston chamber 270 are fluidically coupled via the reservoir inlet 460, the valve chamber inlet/outlet 458, and the piston chamber inlet/outlet 423 only when the valve 456 is in this fill position. The piston 420 is initially at a closed end of the piston chamber 270, such that only a negligible amount of medicament may be in the piston chamber 270. The cam follower pin 438 is in a stable position on the cam track 448, being driven by the piston spring 426 to a point at the intersection of the decreasing radius section 450 and the increasing radius section 454.

As the actuation element or button 268 is moved by the first actuating force $F_1$ applied by the patient on the button 268 from the rest position 600 to the fill end position 602, the rack and gear system rotates the drive shaft 432 clockwise, thereby rotating the ratchet 434 and forcing the ratchet arms 435 to engage the ledges 446. Further, the valve spring 412 starts to be compressed. Additional movement of the actuation element 268 rotates the cam disk 436, translating the follower 438 (and by extension the piston bar 440 and the piston 420) in a horizontal plane as the follower 438 moves along the decreasing radius section 450. The piston 420 is retracted relative to the closed end of the piston chamber 270, creating a pressure drop in the piston chamber 270 and increasing chamber volume for drawing medicament from the bolus reservoir 256 through the reservoir inlet 460, the valve chamber inlet/outlet 458, and the piston chamber inlet/outlet 423 into the piston chamber 270. This movement also begins to compress the piston spring 426. Once the piston 420 is fully retracted, and the piston chamber 270 contains a full dose of medicament, the gap G between the valve contact 410a and the valve 456 is zero, and the follower 438 is at the interface with the constant radius section 452. See FIGS. 9A and 9B.

When the follower 438 is in the decreasing radius section 450 or the constant radius section 452 (i.e., the actuation element 268 has not reached the point of no return 604), each movement of the actuation element 268, either forwards or backwards, is directly linked to the movement of the piston 420. For example, incrementally moving the actuation element 268 forward will further retract the piston 420 (and compress the piston spring 426), filling the piston chamber 270 to the level of the seal 424a on the piston 420. If the actuation element 268 is released, so that it returns to the rest position 600 due to the force of the piston spring 420 and the valve spring 412, the piston spring 426 incrementally forces the piston 420 to empty the piston chamber 270, limited by the position of the actuation element 268. Since the valve 456 is still in the fill position, any medicament emptied from the piston chamber 270 returns to the bolus reservoir 256. Thus, partial doses cannot be delivered to the dosing conduit 276 or the patient. As can be appreciated, controlling the volume of the bolus reservoir 256 limits the number of bolus doses that may be delivered in a given time period, and the volume may be limited to contain only a non-injurious amount of medicament. The volume of the bolus reservoir 256 is a fraction of the volume of the pressurized reservoir 252, for example in a range of up to about 5% typically. In one embodiment, due to the low flow rate between the pressurized reservoir 252 and the bolus reservoir 256, sufficient time will pass before another bolus dose can be delivered by the patient in the event the patient fully drains the bolus reservoir 256. See, for example, U.S. Pat. No. 7,517,335, the disclosure of which is hereby incorporated by reference herein in its entirety. The flow rate can be customized for a particular user, as the use of high-flow capillaries will allow the bolus reservoir 256 to fill more quickly, and the use of low-flow capillaries will restrict the bolus reservoir 256 to fill more slowly.

Figure 9A:
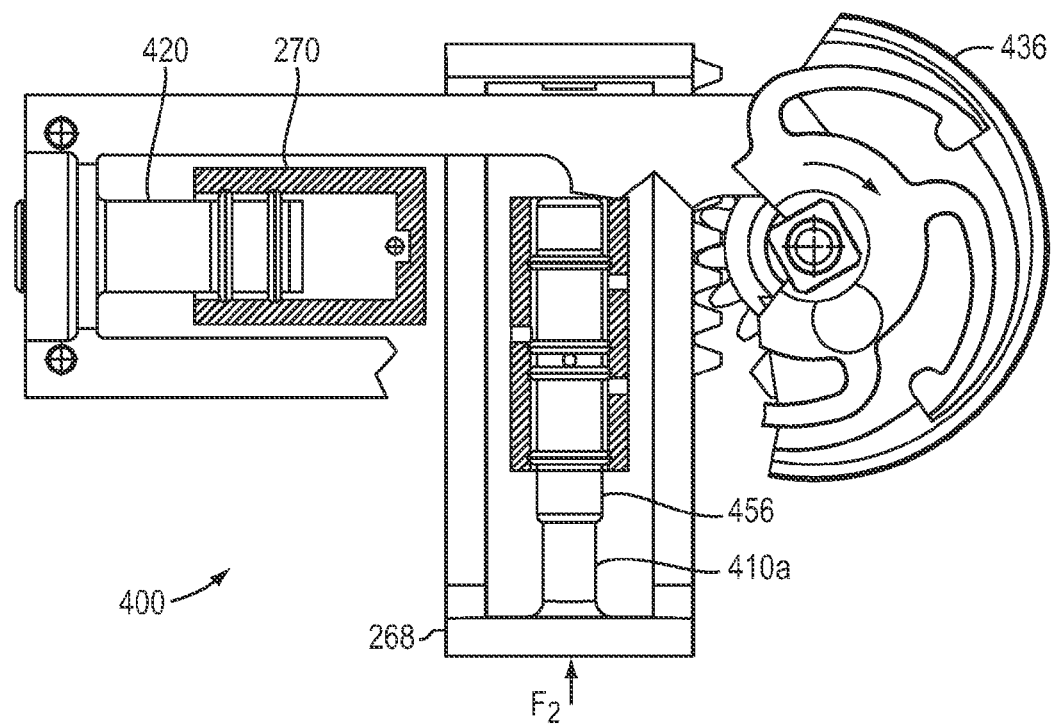
FIG. 9A is a schematic partial plan view of a mechanical pump system with an actuation button at a fill end position, in accordance with one embodiment of the invention.
Figure 9B:
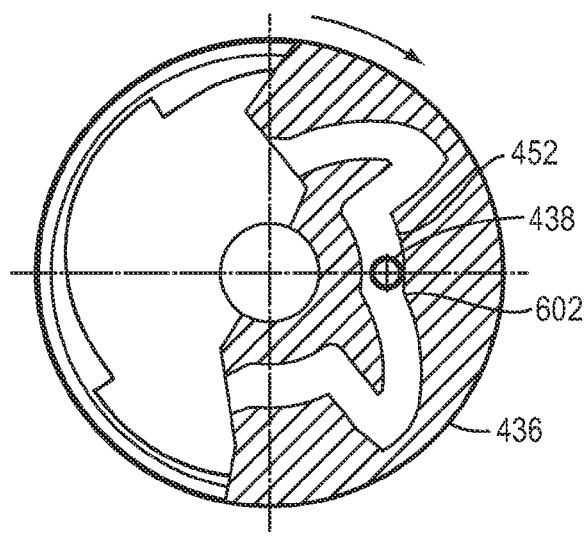
FIG. 9B is a schematic partial cutaway view of a cam disk of the mechanical pump system depicted in FIG. 9A at the fill end position.

FIGS. 9A and 9B depict the mechanical pump system 400 at the end of the first step 502/beginning of the second step 504. The actuation element 268 is at the fill end position 602 and the piston chamber 270 is filled with a full dose, when the valve contact 410a first comes into contact with the valve 456. The valve spring 412 is partially compressed, biasing the actuation element toward the rest position 600. The piston 420 is fully retracted, thereby fully compressing the piston spring 426. The follower 438 is in the constant radius section 452, where movement of the actuation element 268 rotates the cam disk 436, but the follower 438 (and therefore the piston bar 440 and the piston 420) does not translate.

As the actuation element 268 is moved by the second actuating force $F_2$ to a point just before the point of no return 604, the actuation element 268 further compresses the valve spring 410 and begins to shift the valve 456 from a fill position to a dosing position. As described above, though the actuation element 268 and the piston 420 are still coupled to each other, the piston 420 does not translate with movement of the actuation element 268.

Figure 10A:
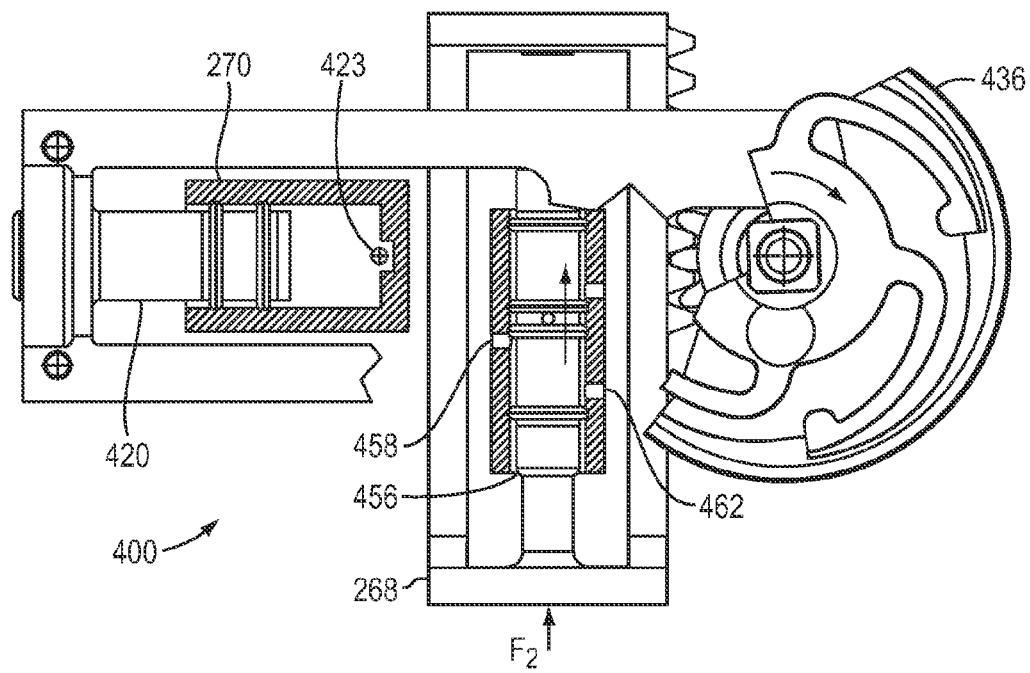
FIG. 10A is a schematic partial plan view of a mechanical pump system with an actuation button approaching a point of no return, in accordance with one embodiment of the invention.
Figure 10B:
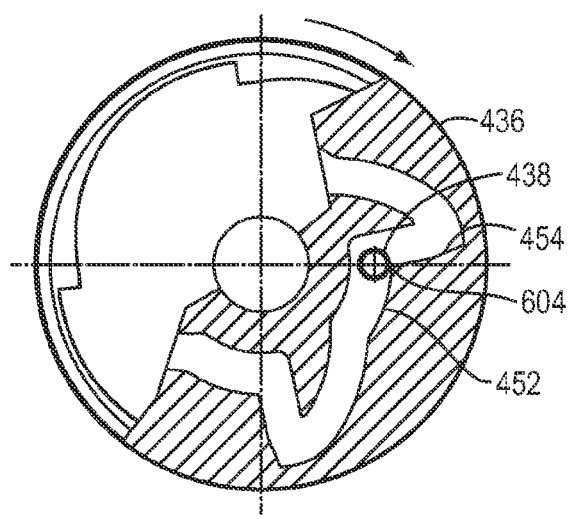
FIG. 10B is a schematic partial cutaway view of a cam disk of the mechanical pump system depicted in FIG. 10A approaching the point of no return.

FIGS. 10A and 10B depict the mechanical pump system 400 at the end of the second step 504/beginning of the third step 506. The actuation element 268 is at a point just before the point of no return 604. The valve 456 has moved into the dosing position, fluidically coupling the piston chamber 270 to the dosing conduit 276 via the piston chamber inlet/outlet 423, the valve chamber inlet/outlet 458, and the dosing conduit outlet 462. The piston chamber 270 and the dosing conduit 276 are only fluidically coupled when the valve 456 is in the dosing position. The follower 438 is just before the point where the constant radius section 452 meets the increasing radius section 454. This point corresponds to the point of no return 604 of the actuation element 268. The piston 420 is still coupled to the actuation element 268, as the follower 438 is still constrained in the constant radius section 452. Release of the button 268 would shift the valve 456 back to the fill position and drain the piston chamber 270 back into the bolus reservoir 256 under the combined action of the piston spring 426 and the valve spring 412.

Figure 11A:
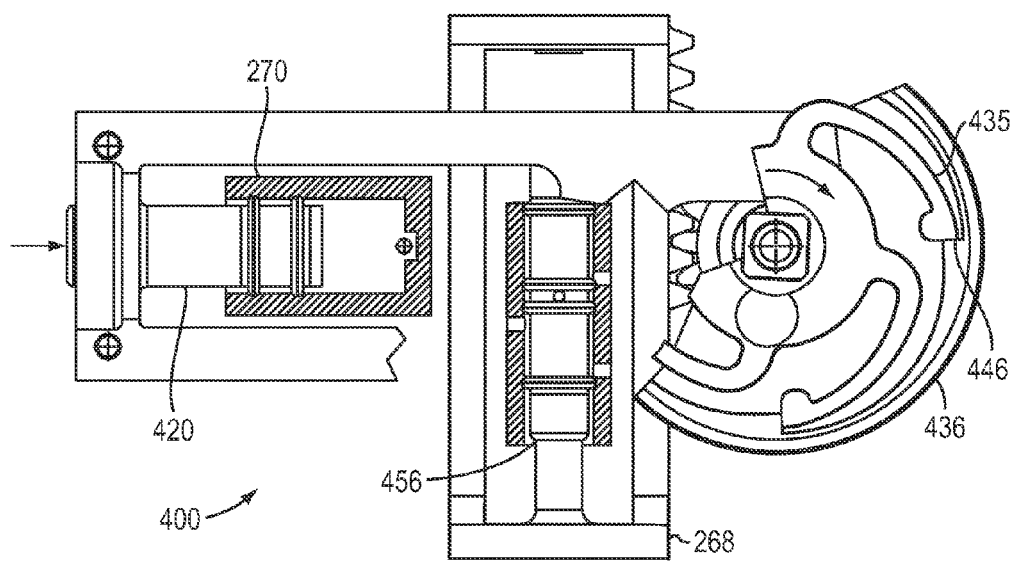
FIG. 11A is a schematic partial plan view of a mechanical pump system with an actuation button past the point of no return, in accordance with one embodiment of the invention.
Figure 11B:
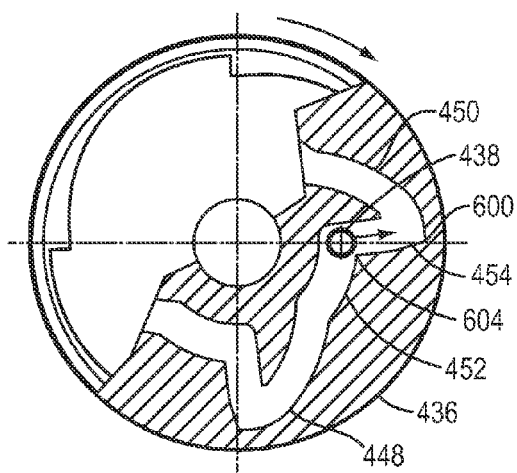
FIG. 11B is a schematic partial cutaway view of a cam disk of the mechanical pump system depicted in FIG. 11A past the point of no return.

FIGS. 11A and 11B depict the mechanical pump system 400 immediately after the actuation element 268 travels beyond the point of no return 604, which is the start of the third step 506. The valve 456 is fully in the dosing position. The follower 438 is just beyond the constant radius section 452, where the track 448 is no longer providing resistance to the piston spring 426. This decouples the piston 420 from the actuation element 268 and allows the piston spring 426 to release, driving the piston 420 toward the closed end of the piston chamber 270. The piston 420 empties the piston chamber 270 of a full dose of medicament, forcing medicament into the dosing conduit 276 through the valve 456. The signaling device 407 sends one of the previously described signals based on feedback from a sensor, that may include detecting that the actuation element 268 traveled beyond the point of no return 604.

In other embodiments, the signaling device 407 may be triggered by alternative means utilizing a rib configured to contact another element at a predetermined point in the process. The signaling device 407 is triggered every time a rib is contacted. For example, a rib may be placed on each of the increasing radius sections 454 just beyond the point corresponding to the point of no return 604 of the actuation element 268 when the piston 420 begins to deliver the bolus dose. The follower 438 contacts one of the ribs only when a full dose is delivered as this is the only time the follower 438 enters the increasing radius sections 454 from the constant radius sections 452. In another embodiment, a rib may be placed on the piston 420 and configured to contact a corresponding element within the piston chamber 270 whenever the piston 420 is either in a fully retracted position, such that the piston chamber 270 is filled with a bolus dose, or in a fully deployed position, such that a bolus dose has been delivered from the piston chamber 270. In yet another embodiment, a rib may be disposed on the actuation element 268 and configured to contact an element at the end of button travel. Another embodiment, utilizing a magnet and a coil, is described below with reference to an interlock mechanism.

As the piston spring 426 releases its stored energy, the piston 420 is decoupled from the actuation element 268. This is depicted as a dashed line in FIG. 7, indicating that the dosing action is independent of the travel of the actuation element 268 (i.e., whether the actuation element 268 is held in position or released, once the piston 420 is decoupled it will complete its process of delivering a full dose of medicament). The cam disk 436 slightly advances such that the ratchet arms 435 are no longer engaged with the ledges 446, and the follower 438 rests at the interface of the decreasing radius section 450 and the increasing radius section 454, at the rest position of the follower 438. The actuation element 268 is limited to the end of travel position, which prevents the ratchet arms 435 from reengaging with the ledges 446 by moving the actuation element 268 forward. The only way to reengage the ratchet 434 with the cam disk 436 and reset the device to deliver another full dose is to return the actuation element 268 to the rest position 600. Any cycling of the actuation element 268 from past the point of no return 604 and a position intermediate with the reengagement position 606 fails to deliver additional medicament through the valve 456. Such cycling is incapable of moving the piston 420 as the ratchet 434 is rotating without engaging the cam disk 436 (which constrains the filling motion of the piston 420). Though the valve 456 may move when the actuation element 268 is cycled in this manner, medicament from the reservoir 256 cannot enter the piston chamber 270 because the piston 420 is disposed at the closed end under the force of the piston spring 426. As fluidic communication between the bolus reservoir 256 and the dosing conduit 276 is precluded, no additional medicament will be delivered until the button 268 is released, the pump 400 reset, and the complete cycle 500 repeated.

Once a dose has been delivered and the actuation element 268 is at the end of travel position, in standard operation the actuation element 268 is returned to the rest position 600. The actuation element 268 may be moved automatically by the valve spring 412. As the actuation element 268 is moving back to the rest position 600, the valve contact 410b contacts the valve 456 (shown in FIGS. 12A and 13A) and moves the valve 456 from the dosing position to the fill position. The piston spring 426 drives the piston 420 at a greater rate of speed than the valve spring 412 moves the valve 456 (via the actuation element 268) to ensure that a full bolus dose is delivered before the valve 456 shifts from the fill to the dosing position in the event the actuation element 268 is immediately released once it passes the point of no return 604. Further, for the same reasons as described above with respect to FIG. 7B, a user is unlikely to be able to react quickly enough to move the actuation element 268 past the fill end position 602 without holding the actuation element 268 for a sufficient moment of time at the end of travel position after the piston 420 has delivered the bolus dose. The force required to move the actuation element 268 past the fill end position 602 may be approximately 5-15 N, and is just under 8 N in the embodiment depicted in FIG. 7B.

In another embodiment, an optional interlocking mechanism 480 is included to retain the actuation element 268 beyond the point of no return 604 (and thus the valve 456 in the dosing position), only releasing the actuation element 268 to return to the rest position 600 once the piston 420 reaches the closed end of the piston chamber 270 and the full dose has been delivered, as depicted in FIGS. 15A1-18B. In one embodiment, the interlock 480 includes a resilient cantilevered element 482, a detent 484, and a release 486. The resilient element 482 extends outwardly from a side of the actuation element 268. One end of the resilient element 482 is attached to the actuation element 268 to act as a hinge, allowing the resilient element 482 to deflect easily toward the actuation element 268 and to return to its non-deflected position extending away from the actuation element 268. The resilient element 482 also optionally includes a magnet 488 at its distal end. The detent 484 is fixed to the base 408 and configured to contact the resilient element 482. One corner of the detent 484 is chamfered to deflect the resilient element 482 without binding. The release 486 is attached to the piston bar 440 and is configured to move along or near a surface of the detent 484. Distal ends of the release 486 and the detent 484 substantially align when the piston 420 is at the closed end of the piston chamber 270. The distal end of the release 486 may also include a pickup 490, such as a coil, a reed relay, or a GMR sensor.

As the actuation element 268 moves from the fill end position 602 to the point of no return 604, the resilient element 482 contacts the chamfered edge of the detent 484. The detent 484 deflects the resilient element 482 toward the actuation element 268 until the resilient element 482 passes the detent 484. Once past the detent 484, the resilient element 482 returns to its un-deflected state. Despite the bias of the compressed valve spring 412, the actuation element 268 may not be returned to the rest position 600 because of the interference between the resilient element 482 and the detent 484 (see FIGS. 15A2 and 15B). Because the piston 420 is in the retracted position, and the release 486 is linked to the piston through the piston bar 440, the resilient element 482 will not be deflected to pass the detent 484 until the piston 420 delivers a full dose of medicament. As the actuation element 268 passes the point of no return 604, the piston spring 426 forces the piston 420 to empty fully and quickly the medicament from the piston chamber 270. As the piston bar 440 reaches its end of travel, the release 486 moves to the end of the detent 484, deflecting the resilient element 482 and allowing the actuation element 268 to return to the rest position 600 (see FIGS. 16A and 16B) due to the bias of the valve spring 412. The resilient element 482 is prevented from reengaging the backside of the detent 484 following delivery of a dose because of the location of the release 486, unless the piston bar 440 is retracted.

The coil 490 may be connected to the signaling device 407 to indicate when the coil 490 approaches the magnet 488 following delivery of a dose. The signaling device 407 may detect the electrical pulse generated when the magnet 488 and the coil 490 are in close proximity. The signaling device 407 may be programmed to differentiate between a high, narrow pulse which would be generated when the piston spring 426 releases its energy following decoupling, which necessarily delivers a dose of medicament, and a lower, longer pulse which could be generated by cycling the actuation element 268 after delivery of a dose but prior to reengaging the system. In another embodiment also depicted in FIG. 15B, a magnet 489 may be placed on the piston chamber 270 in a location spaced from the closed end, such that the coil 490 and the magnet 489 come into close proximity only when the piston chamber 270 is filled and a dose is about to be delivered. A number of related coil and magnet positions may be used to detect when the piston frame 440 is in this position. In this embodiment, the signaling device 407 may be configured to require two sequential pulses (first from the proximity of the piston chamber magnet 489 and the coil 490, and then from the proximity of the resilient element magnet 488 and the coil 490) before signaling that a dose has been delivered. This prevents a signal from being delivered when the actuation element 270 is cycled following delivery of a dose but prior to reengaging the system, and also does not require the signaling device 407 to analyze the strength and length of the particular pulse. When a magnet and a pickup are used to deliver a pulse, the tolerances must be precise enough to ensure the magnet and the pickup come into a range of proximity, but this scheme does not necessarily require extraordinary precision. Water-proof electrical connections or a limited impedance and voltage range tolerant to both wet and dry electrical connections may be used to ensure accurate and consistent transmission of an electrical signal from the disposable subsystem to the reusable subsystem. Also, flexible, low-friction, or no friction electrical connections may be used when the magnet and/or the pickup are located on moving parts.

Figure 17A:
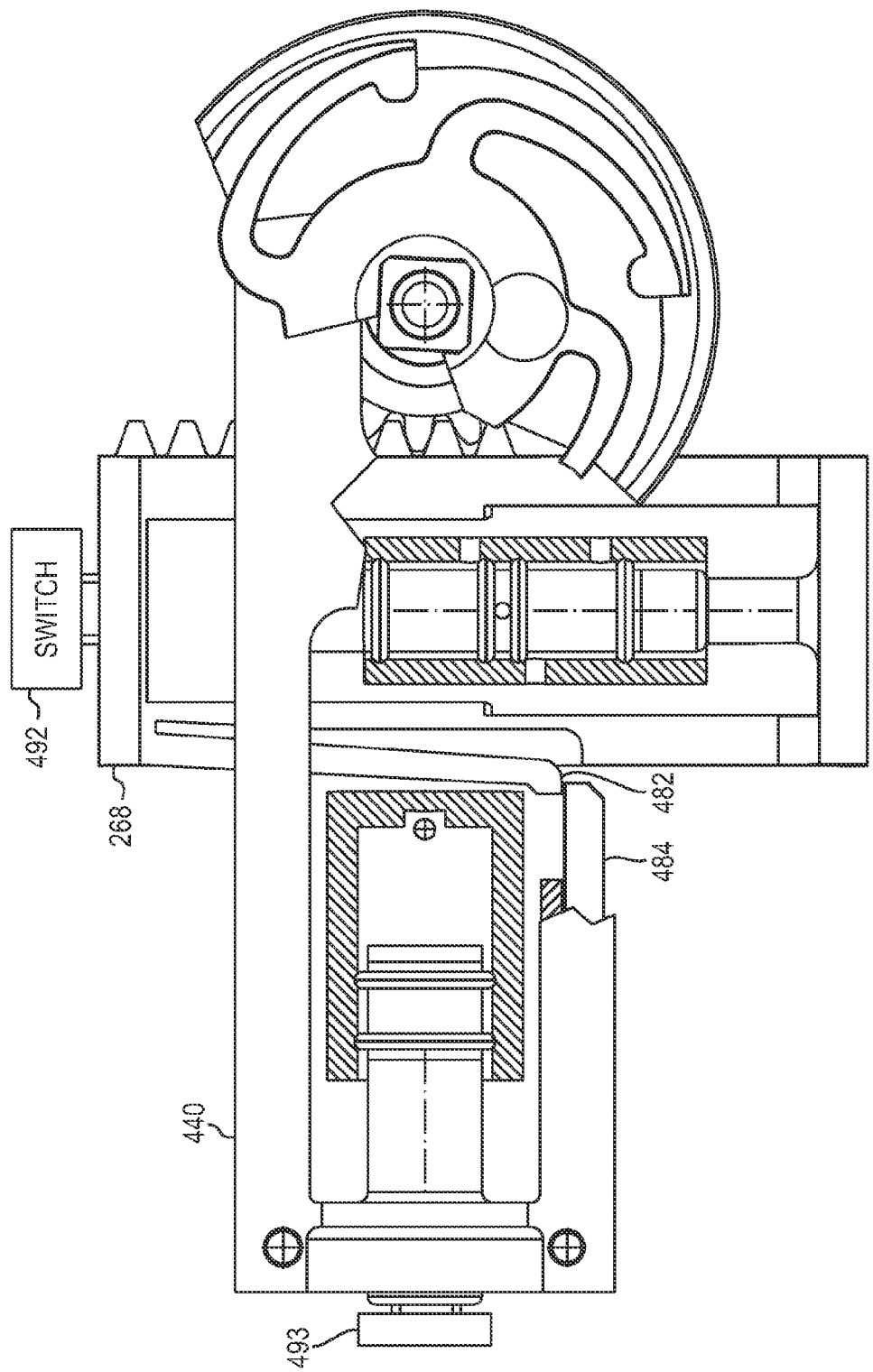
FIG. 17A is a schematic partial plan view of a mechanical pump system with an actuation button approaching a point of no return, an interlock, and a switch, in accordance with one embodiment of the invention.

In other embodiments, the signaling device 407 may be triggered by depressing a switch 492, for example located at the end of travel of the actuation element 268 (as depicted in FIGS. 17A and 17B), though the switch 492 may also be placed at other locations. The switch 492 may be any of a number of types of switches, such as an OTS switch. The switch 492 may be located inside a disposable subsystem with electrical leads connecting it to a reusable subsystem. The switch 492 may be made with low-cost parts and the electrical leads may be connected with waterproof connections, or the switch may work in an impedance and signal voltage range tolerant to both wet and dry electrical connections. Alternatively, the switch 492 may be located inside a reusable subsystem with a waterproof window through which the switch 492 may be activated, adding no additional parts or assembly when the housing is made with 2-shot molded parts. The signaling device 407 may be triggered by either closing or opening the switch 492. When the optional resilient element 482 and the detent 484 are used, there may be a limited distance, for example approximately 0.1 mm to 0.2 mm, between the end of the actuation element 268 and the switch 492 when the resilient element 482 is resting on the detent 484. Because of some of the tight tolerances, a lever-arm amplification may be used. To prevent additional signal deliveries from cycling the actuation element 268 before reengaging the system, an additional switch 493 may be located near the end of travel of the piston frame 440. Contacting the piston frame switch 493 may "arm" the signal, and then activating the actuation element switch 492 would deliver (and "disarm") the signal. No signal would be delivered if the signal is not "armed." This avoids false dose counts due to cycling the actuation element 268 without delivery of medicament.

Figure 18A:
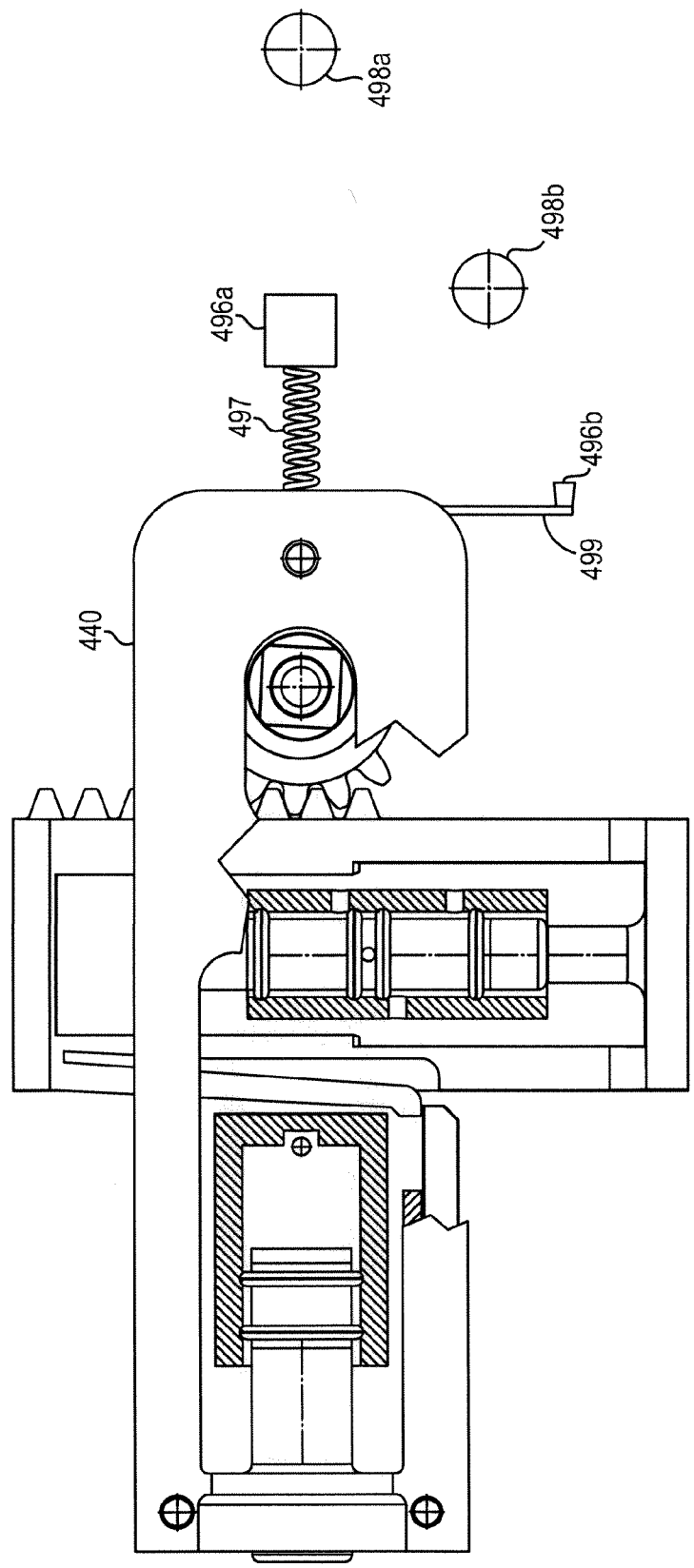
FIG. 18A is a schematic partial plan view of a mechanical pump system with an actuation button approaching a point of no return, an interlock, and an impulse mechanism, in accordance with one embodiment of the invention.
Figure 18B:
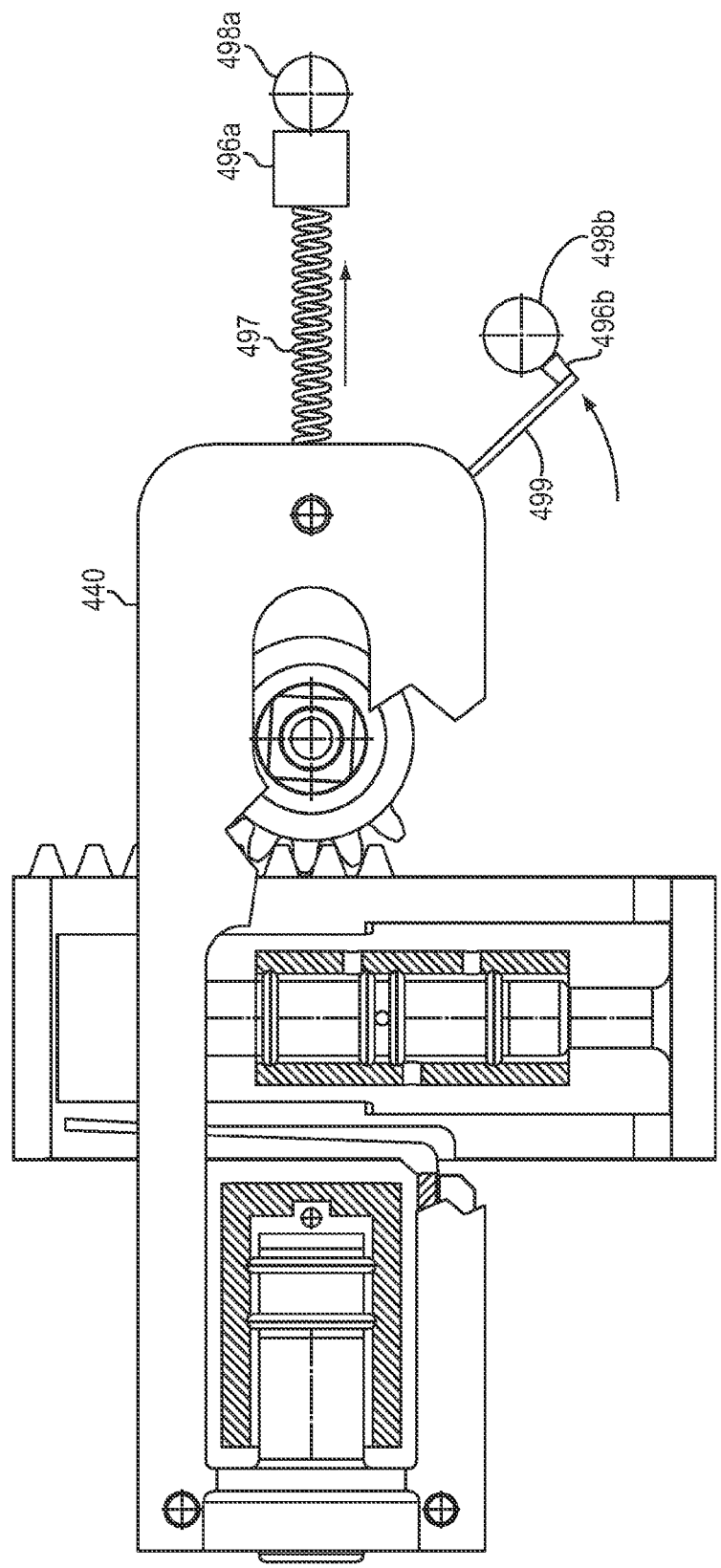
FIG. 18B is a schematic partial plan view of the mechanical pump system of FIG. 18A immediately after delivering a dose.

In still other embodiments, the rapid movement of the piston frame 440 during the delivery of a dose may generate an impulse which is transferred to a magnet. Two different embodiments are depicted in FIGS. 18A and 18B: a first embodiment where a magnet 496*a* is mounted on the end of an impulse spring 497 mounted (or formed) on an end of the piston frame 440; and a second embodiment where a magnet 496b is mounted on a resilient cantilevered arm 499 attached to (or formed on) the end of the piston frame 496. In both embodiments, when the piston frame 440 stops at the end of travel after delivering a dose, the magnet 496 will continue moving due to extension of the spring 497 or the magnet 496b will continue moving due to bending of the resilient cantilevered arm 499 until the magnet(s) come into close proximity with a resistive pickup 498a, 498b. The pickup 498 may be any of a number of devices capable of generating an electrical impulse based on the changing proximity of a permanent magnet, such as a coil, a reed relay, and a GMR sensor. The pickup 498 may be located in a reusable section, while low cost passive parts (e.g., magnets, pieces of high permittivity material, an interrupter for triggering an optical switch, a lever for triggering a switch, etc.) may be located in a disposable section. The pickup 498 may be calibrated to generate an electrical impulse when the permanent magnet is in a wide proximity, reducing the need for tight tolerances. Detecting only when the piston frame exceeds a threshold velocity and associated deceleration (i.e., change in velocity) at end of travel ensures that the signaling device 407 is only triggered when a dose is delivered. False signals and counts are not delivered when cycling without resetting the system, because the piston frame 440 will not reach that threshold velocity until forced by the piston spring 426 to deliver the full dose.

In another embodiment, the cam disk 436 may include ribs 487 (depicted in FIGS. 15A2 and 16A2) on the exterior surface, approximately aligned with the ledges 446. A sensor, such as an optical or a mechanical sensor, may detect when the ribs 487 cross the axes 491. This only occurs when the actuation element 268 moves past the point of no return 604, delivering a dose and completing the quarter turn advance of the cam disk 436. The ribs 487 on the cam disk 436 do not regress counter-clockwise across the axes 491, only crossing again on the next quarter turn of the cam disk 436 (i.e., when a next dose is delivered).

Figure 12A:
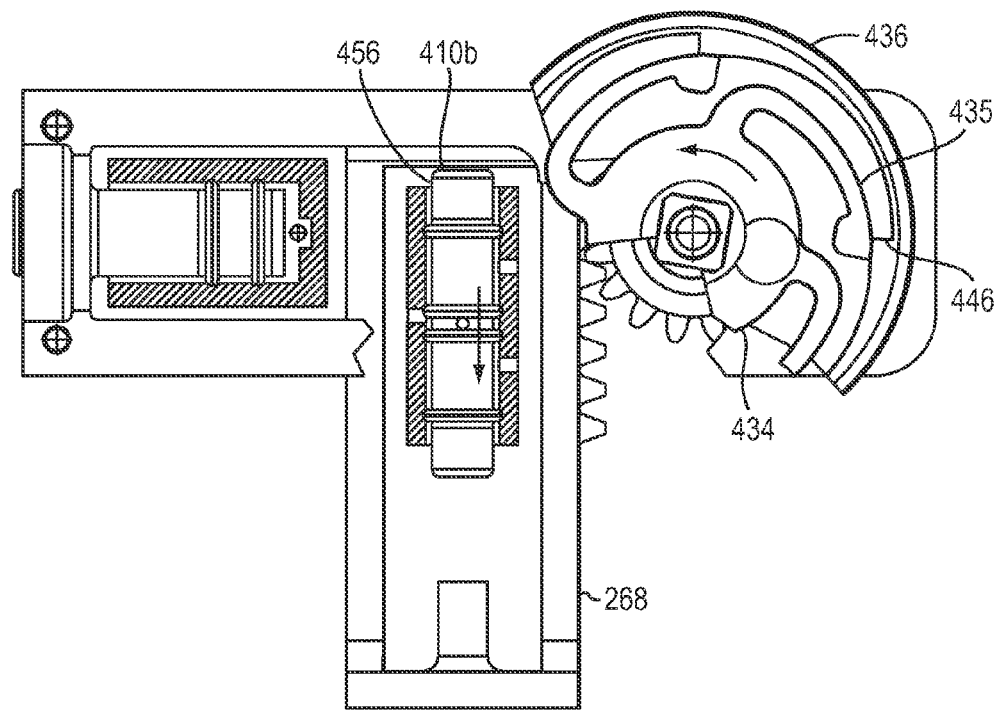
FIG. 12A is a schematic partial plan view of a mechanical pump system with an actuation button just before a reengagement position, in accordance with one embodiment of the invention.
Figure 12B:
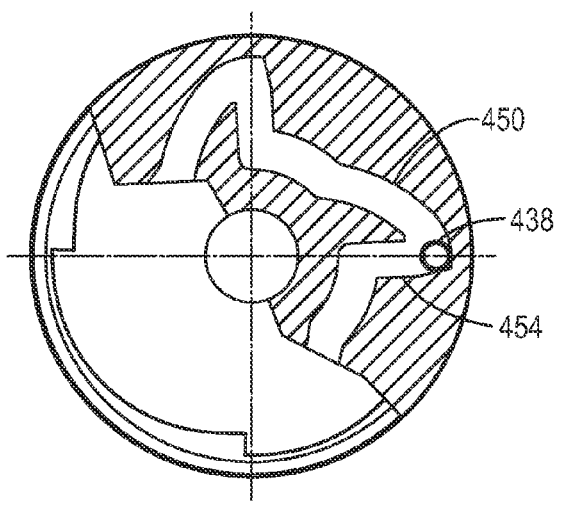
FIG. 12B is a schematic partial cutaway view of a cam disk of the mechanical pump system depicted in FIG. 12A just before the reengagement position.
Figure 13A:
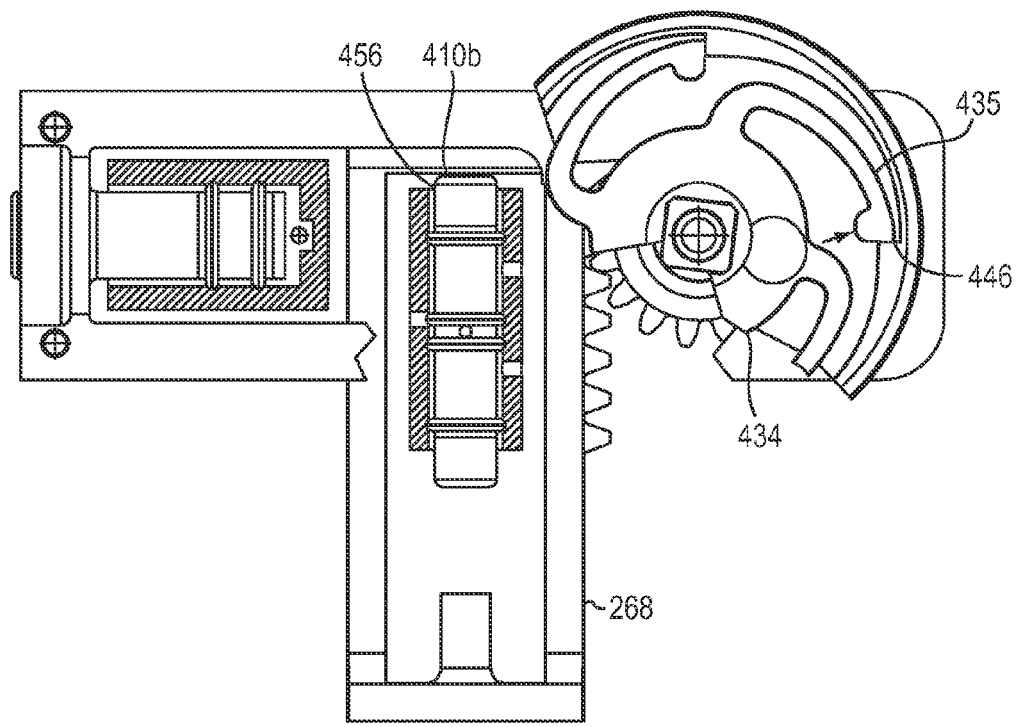
FIG. 13A is a schematic partial plan view of a mechanical pump system with an actuation button past the reengagement position, in accordance with one embodiment of the invention.
Figure 13B:
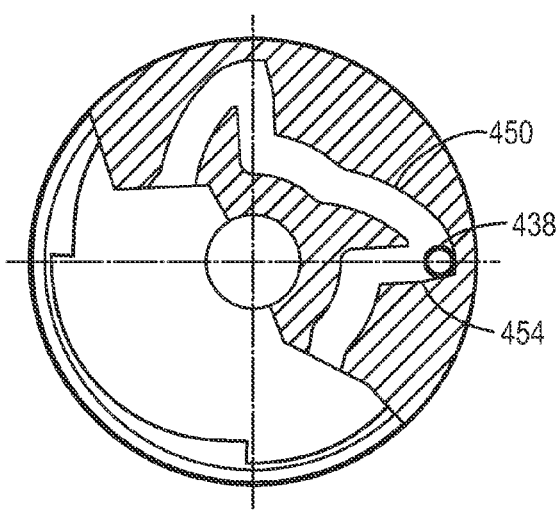
FIG. 13B is a schematic partial cutaway view of a cam disk of the mechanical pump system depicted in FIG. 13A past the reengagement position.

FIGS. 12A and 12B depict the mechanical pump system 400 just before the actuation element 268 reaches the reengagement position 606. As the actuation element 268 moves toward the reengagement position 606, the ratchet 434 moves counterclockwise while the cam disk 436 remains stationary with the follower resting at the intersection of the decreasing radius section 450 and the increasing radius section 454. When the actuation element 268 is near the reengagement position 606, the ratchet arms 435 are slightly deflected inward by the ledges 446. As the actuation element 268 is moved past the reengagement position 606, as depicted in FIGS. 13A and 13B, the ratchet arms 435 return to their radially extended state, allowing for reengagement with the ledges 446 when the ratchet 434 is next moved clockwise. This recouples the motion of the piston 420 with the motion of the actuation element 268. When the actuation element 268 is back in the rest position 600, all of the components of the mechanical pump system 400 are back in their original position as depicted in FIGS. 8A and 8B, except for the cam disk 436 which is functionally in the same position, but has advanced a quarter turn.

The various components utilized in the device described herein may be metal, glass, and/or any type of polymer suitable for sterilization and useful for delivering insulin or other medicaments. Polyurethane, polypropylene, polystyrene, nylon, and others, are contemplated for use, as are stainless steel and other medical-grade metals. More specifically, medical-grade plastics may be utilized for the dosing conduit itself, as well as other components that contact or otherwise penetrate the body of the patient.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The compositions, components, and functions can be combined in various combinations and permutations, to achieve a desired result. For example, all materials for components (including materials not necessarily previously described) that are suitable for the application are considered within the scope of the invention. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A mechanical pump system comprising:
   an actuation element;
   a direct drive piston system comprising:
      a piston chamber;
      a piston disposed within the piston chamber;
      a direct drive coupled to the actuation element for moving the piston relative to the piston chamber when the actuation element moves from a rest position to a fill end position to fill incrementally the piston chamber with medicament; and
      a piston spring directly coupled to the piston for constantly biasing the piston to empty the piston chamber; and
   a lost motion valve system comprising:
      a valve chamber; and
      a valve disposed within the valve chamber, wherein the valve is displaced from a fill position to a dosing position by contact with the actuation element after the actuation element travels beyond the fill end position.

2. The mechanical pump system of claim 1, wherein the actuation element comprises a manually operable button.

3. The mechanical pump system of claim 1, wherein the direct drive comprises at least one of a rack and gear system and a cam and follower system.

4. The mechanical pump system of claim 3, wherein the direct drive comprises both the rack and gear system and the cam and follower system.

5. The mechanical pump system of claim 4, wherein the cam and follower system comprises a cam disk with a track for constraining motion of a piston bar coupled to the piston.

6. The mechanical pump system of claim 5, wherein the track comprises a point corresponding to a point of no return of the actuation element beyond which the piston becomes decoupled from the actuation element.

7. The mechanical pump system of claim 6, wherein the direct drive further comprises a ratchet element mating with the cam disk to decouple the actuation element from the piston.

8. The mechanical pump system of claim 7, wherein the cam disk comprises a ledge for mating with the ratchet element to recouple the actuation element to the piston at a reengagement position.

9. The mechanical pump system of claim 8, wherein the ratchet element and the cam disk are configured such that cycling of the actuation element from past the point of no return to a position intermediate with the reengagement position fails to deliver medicament through the valve.

10. The mechanical pump system of claim 1, wherein the actuation element forms a gap with the valve, such that the valve does not move when the actuation element moves from the rest position to the fill end position.

11. The mechanical pump of claim 1 further comprising a return spring for biasing the actuation element toward the rest position.

12. The mechanical pump of claim 1, wherein the valve fluidically couples a reservoir and the piston chamber only when the valve is in the fill position.

13. The mechanical pump system of claim 1, wherein the valve fluidically couples the piston chamber and a dosing conduit only when the valve is in the dosing position.

14. The mechanical pump system of claim 1, wherein the valve system is configured to preclude direct fluidic communication between a reservoir and a dosing conduit.

15. The mechanical pump system of claim 1, wherein the valve system further comprises at least one fluidic outlet for dumping medicament if pressure exceeds a predetermined limit.

16. The mechanical pump system of claim 1, wherein the piston chamber contains a full dose of medicament when the actuation element is at the fill end position, thereby precluding delivery of a partial dose of medicament to a dosing conduit.

17. The mechanical pump system of claim 1, wherein moving the actuation element from the rest position to the fill end position compresses the piston spring and an actuation element return spring, resulting in a first increasing reaction force, and moving the actuation element past the fill end position toward the point of no return compresses further solely the return spring.

18. The mechanical pump system of claim 1 further comprising a signaling device for delivering a signal as a full dose of medicament is delivered.

19. A mechanical pump system comprising:
an actuation element;
a direct drive piston system comprising:
    a piston chamber;
    a piston disposed within the piston chamber;
    a direct drive coupled to the actuation element for moving the piston relative to the piston chamber when the actuation element moves from a rest position to a fill end position to fill incrementally the piston chamber with medicament, wherein the direct drive comprises at least one of a rack and gear system and a cam and follower system; and
    a piston spring directly coupled to the piston for constantly biasing the piston to empty the piston chamber; and
a lost motion valve system comprising:
    a valve chamber; and
    a valve disposed within the valve chamber,
wherein the valve is displaced from a fill position to a dosing position after the actuation element travels beyond the fill end position.

20. The mechanical pump system of claim 19, wherein the direct drive comprises both the rack and gear system and the cam and follower system.

21. The mechanical pump system of claim 20, wherein the cam and follower system comprises a cam disk with a track for constraining motion of a piston bar coupled to the piston.

22. The mechanical pump system of claim 21, wherein the track comprises a point corresponding to a point of no return of the actuation element beyond which the piston becomes decoupled from the actuation element.

23. The mechanical pump system of claim 22, wherein the direct drive further comprises a ratchet element mating with the cam disk to decouple the actuation element from the piston.

24. The mechanical pump system of claim 23, wherein the cam disk comprises a ledge for mating with the ratchet element to recouple the actuation element to the piston at a reengagement position.

25. The mechanical pump system of claim 24, wherein the ratchet element and the cam disk are configured such that cycling of the actuation element from past the point of no return to a position intermediate with the reengagement position fails to deliver medicament through the valve.

* * * * *